United States Patent [19]

Nunan

[11] Patent Number: 4,868,843
[45] Date of Patent: Sep. 19, 1989

[54] MULTILEAF COLLIMATOR AND COMPENSATOR FOR RADIOTHERAPY MACHINES

[75] Inventor: Craig S. Nunan, Los Altos Hills, Calif.

[73] Assignee: Varian Associates, Inc., Palo Alto, Calif.

[21] Appl. No.: 72,814

[22] Filed: Jul. 10, 1987

Related U.S. Application Data

[63] Continuation-in-part of Ser. No. 905,988, Sep. 10, 1986, abandoned, which is a continuation of Ser. No. 168,621, Mar. 7, 1988.

[51] Int. Cl.$^4$ .............................................. G21K 1/04
[52] U.S. Cl. ..................................... 378/152; 378/65; 378/151; 250/505.1
[58] Field of Search .................. 378/147, 65, 148, 149, 378/150, 151, 152, 153, 157, 158; 250/390 I, 505.1

[56] References Cited

U.S. PATENT DOCUMENTS

| | | |
|---|---|---|
| 2,844,736 | 7/1958 | Johns et al. . |
| 2,881,329 | 4/1959 | Peyser . |
| 2,959,680 | 11/1960 | Green . |
| 3,755,672 | 8/1973 | Edholm et al. ...................... 378/159 |
| 4,246,488 | 9/1981 | Hura . |
| 4,365,341 | 12/1982 | Lam ...................................... 378/65 |
| 4,463,266 | 7/1984 | Brahme . |
| 4,464,778 | 8/1984 | Goldmann .......................... 378/151 |
| 4,672,212 | 6/1987 | Brahme . |
| 4,672,652 | 6/1987 | Hüttnrauch et al. ............... 378/151 |
| 4,726,046 | 2/1988 | Nunan .................................. 378/65 |
| 4,754,147 | 6/1988 | Maughan et al. . |
| 4,794,629 | 12/1988 | Pastyr et al. .......................... 378/65 |

OTHER PUBLICATIONS (1) Perry et al., "Computer Control of Patient and Machine Parameters in Radiation Therapy", *Proceedings Seventh International Conference on the Use of Computers in Radiation Therapy*, The Japan Radiological Society, 1981, Sep. 22-26, 1980, pp. 21-27.

(2) Matsuda et al., "Computer Controlled Multi-Leaf Conformation Radiotherapy", *Nippon Acta Radiologica*, Oct. 25, 1981.

(3) Matsuoka et al., "Computer Controlled Multi-Leaf Conformation Radiotherapy", Tokyo Metropolitan Komagome Hospital.

Chin et al., "A Computer-Controlled Radiation Therapy Machine for Pelvic and Para-Aortic Nodal Areas", *Int. J. Radiation Oncology, Biol. Phys.*, 7, pp. 61-70, 1981.

Davy et al., "Conformation Therapy Using the Tracking Cobalt Unit", *Brit. J. Radiology*, 48, pp. 122-130, 1975.

Ueda, "Application of Conformation Radiotherapy and its Technical Problems", *Proc. Japanese Radiation Technology Society*, 32nd meeting, pp. 1-46, Sep. 1976.

Bess, L., Ovadia, J., Valassis, J., "External Beam Current Monitor for Linear Accelerators", *Rev. Sci. Instr.*, vol. 30, pp. 985-988, 1959.

Menke, J. L., "Beam Monitoring at the NBS Linac-Energy, Positioning, Current, Charge", *I.E.E.E. Trans on Nuclear Science*, No. 3, pp. 921-922.

Mohan et al., "Use of Fast Fourier Transforms in Calculating Dose Distributions for Irregularly Shaped Fields for Three-Dimensional Treatment Planning", *Med. Phys.*, 14, pp. 70-77, 1987.

*Primary Examiner*—Carolyn E. Fields
*Assistant Examiner*—David Porta
*Attorney, Agent, or Firm*—Stanley Z. Cole; Peter J. Sgarbossa; Kenneth L. Warsh

[57] ABSTRACT

In a radiation therapy machine it is desirable to produce irregular radiation field shapes in order to shield critical organs not invaded by the tumor. A system is provided using a multileaf collimator formed of a multiplicity of heavy metal bar leaves driven relative to a pair of frames which are driven relative to jaws of a rectangular field collimator. A multiplicity of compensators, one attached to each leaf on one of the pair of frames is used to adjust the local intensity of the radiation within the field. The x-ray beam is limited to a fan with the jaws, the ends and selected parts of the fan are blocked by the multileaf collimator, and the intensity within various portions of the remaining beam is adjusted with compensators. The field of the fan beam is dynamically controlled by these means while the patient table is moved perpendicular to the plane of the fan beam.

26 Claims, 17 Drawing Sheets

FIG.2
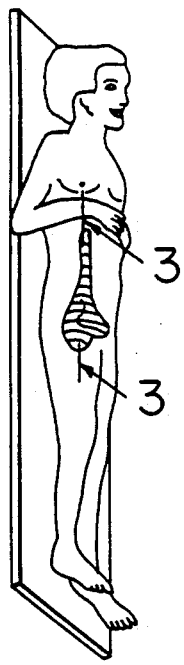
FIG.3
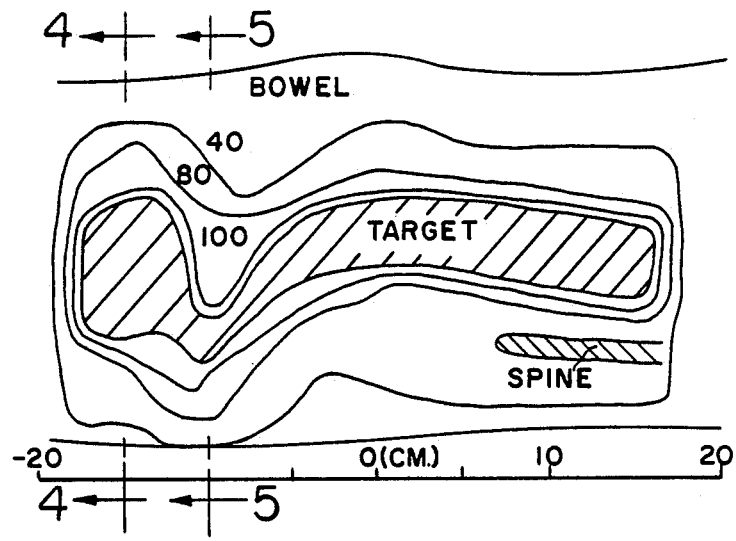
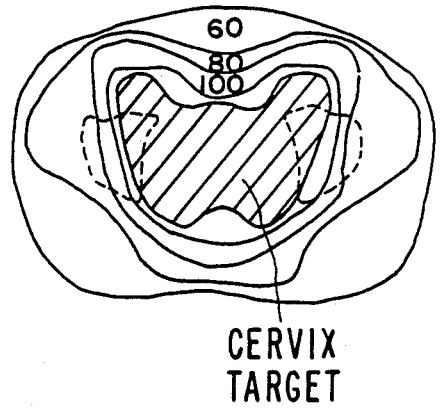
CERVIX
TARGET
FIG.4
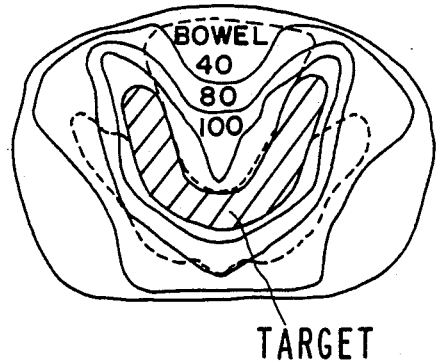
TARGET
FIG.5

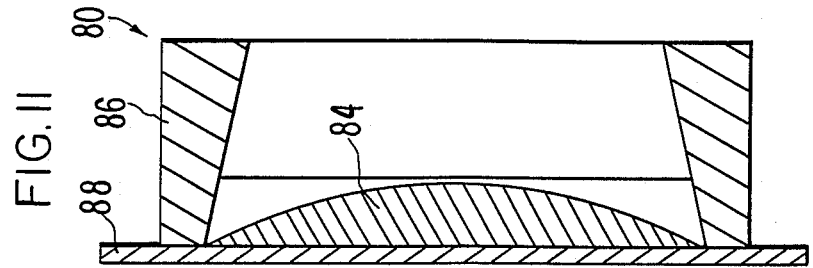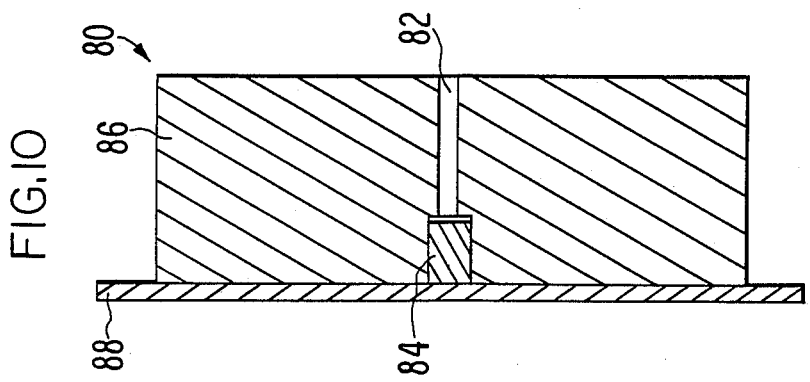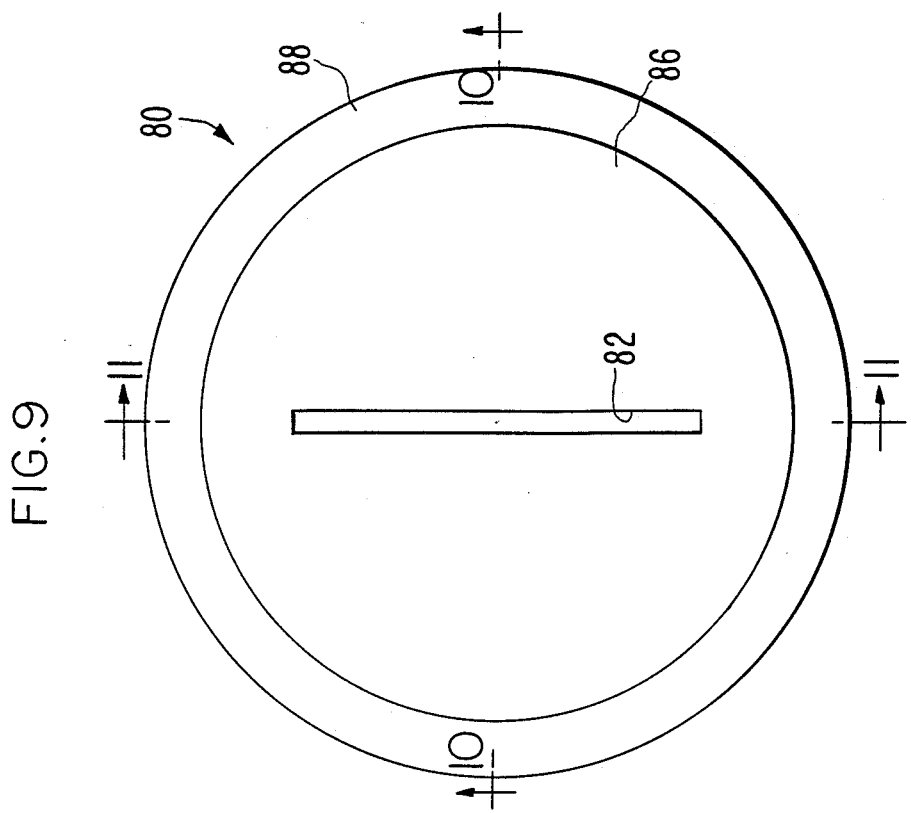

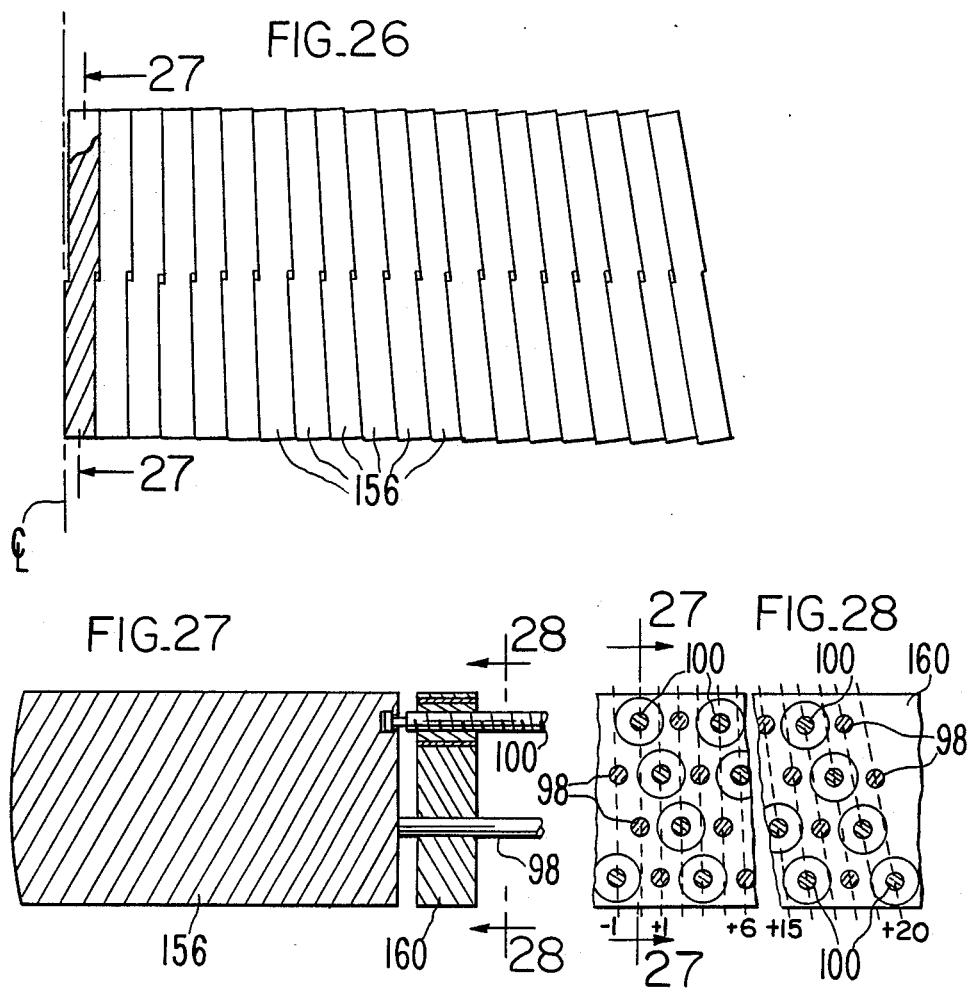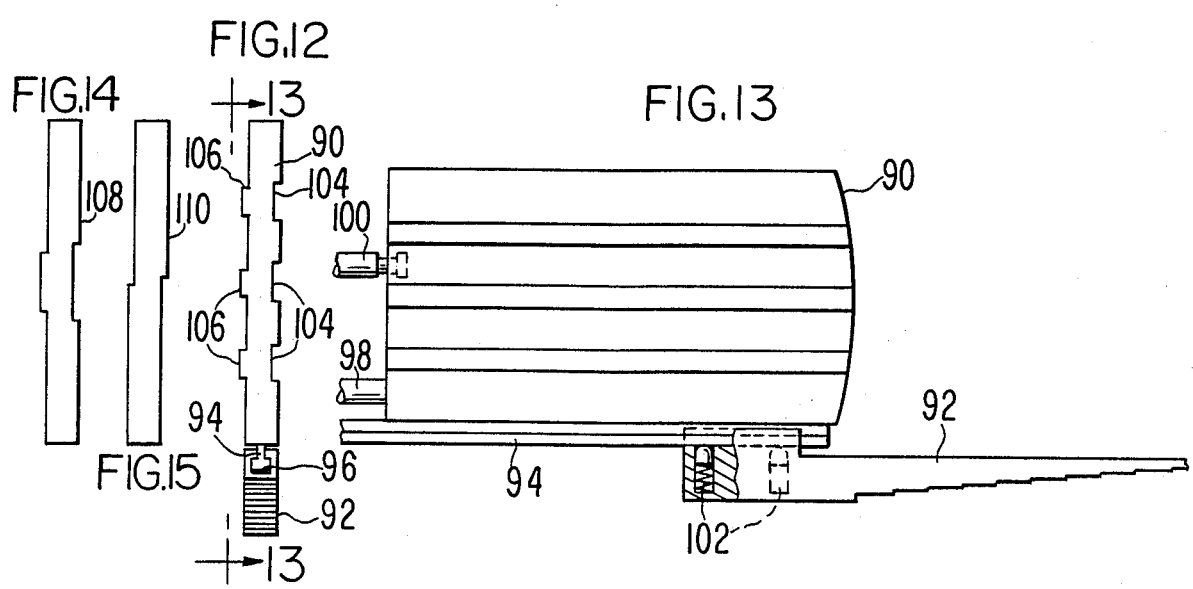

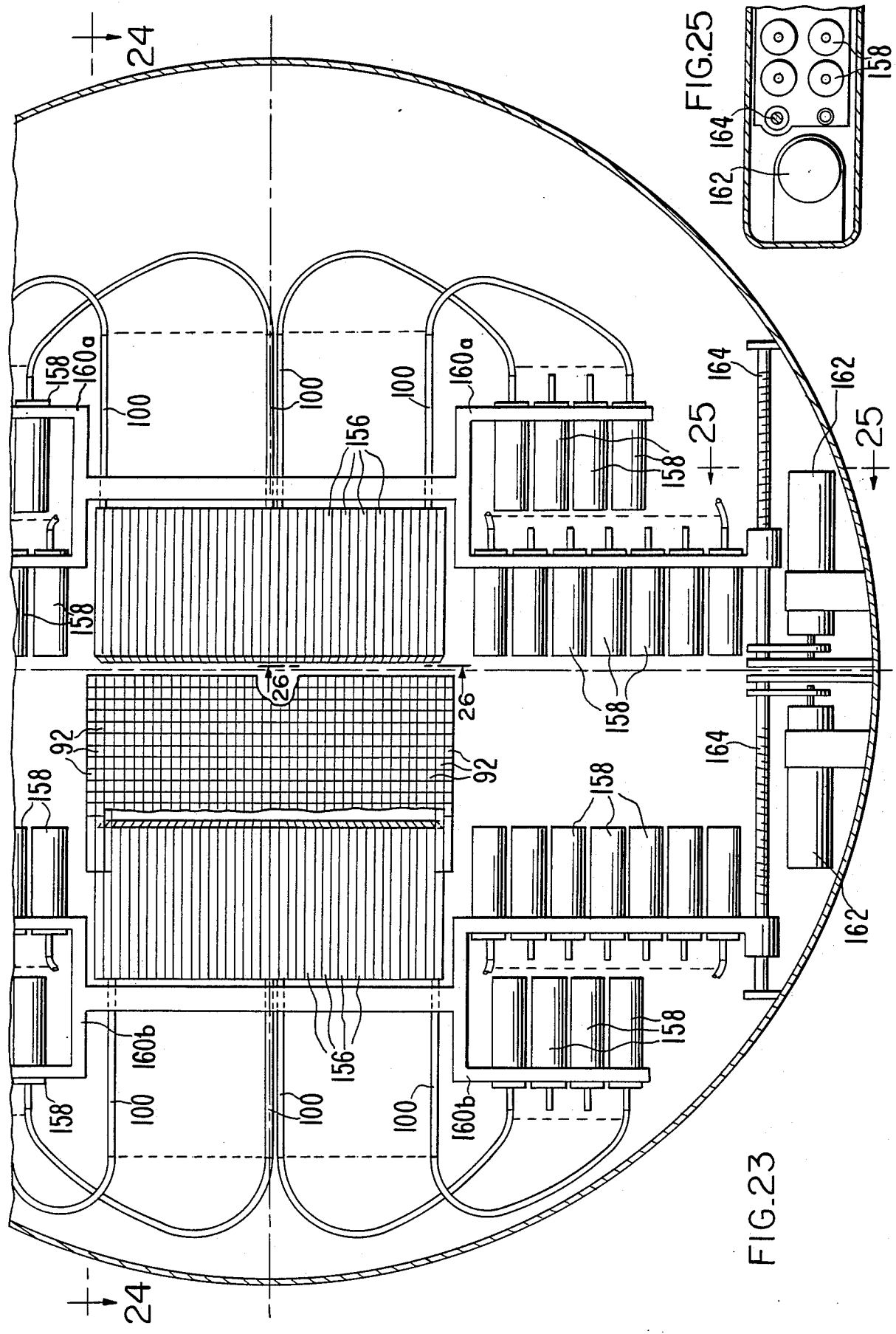

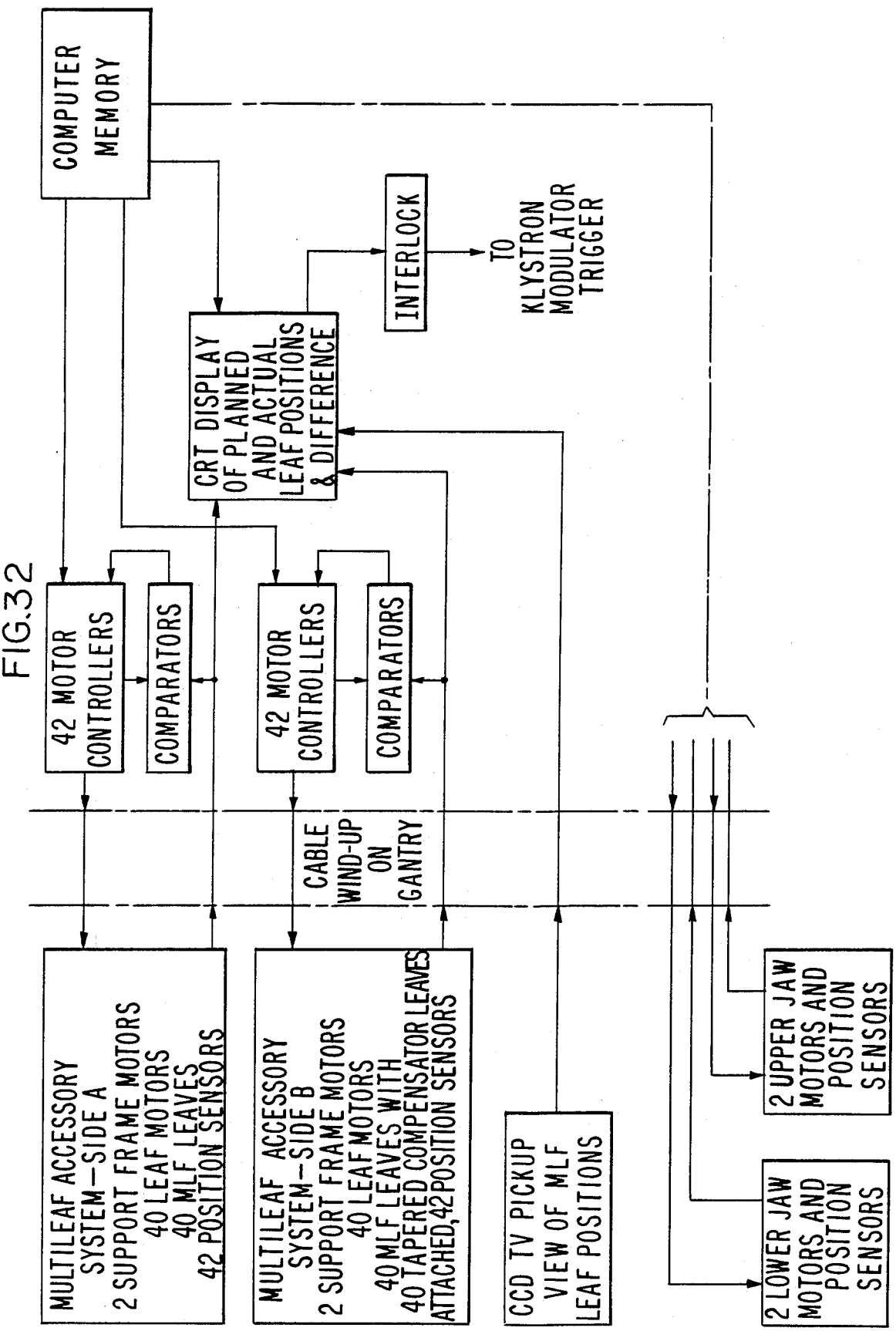

MULTILEAF COLLIMATOR AND COMPENSATOR FOR RADIOTHERAPY MACHINES

This application is a continuation-in-part of U.S. application No. 168,621, filed Mar. 7, 1988, which is a continuation of U.S. application No. 905,988, filed Sept. 10, 1986 now abandoned.

FIELD OF THE INVENTION

This invention pertains to an apparatus and method for radiation treatment employing shaping and dynamic control of spatial distribution of intensity of the radiation field in a radiotherapy machine and in the application of such radiation in a selective manner to living biological materials including human patients in patient therapy for cancer treatment.

BACKGROUND OF THE INVENTION

Conventional x-ray treatment of a tumor in a patient is carried out by planning the radiation angles and dosage by taking into consideration safety factors in respect to the patient's organs which would be in the path of the beam. The treatment plan assumes that the treatment equipment has certain capabilities. Accordingly, the current treatment practice assumes that the machine can cause a beam of selected rectangular shape and intensity to intersect a central fixed point in space from any solid angle. Therefore, the positioning of the patient and the use of multiple positions and multiple beam directions enable one to obtain integrated high doses on selected areas while maintaining low irradiation of other organs. Heretofore, control of the outline of the cross-section of the x-ray beam was accomplished by using jaw devices and control of the intensity of the beam was possible by using absorber plates or accelerator energy controls which provide uniform intensity across the beam cross-section. Irregular shape field boundaries are then obtained by mounting shadow blocks on a shadow tray and irregular intensity across the cross-section is obtained by use of wedge filters or compensating filters (which are shaped pieces of metal), all of which are inserted between the jaws and the patient. These devices naturally have to be changed at every angle.

My invention permits an entirely new method of treatment which eliminates the need for shadow blocks, wedge filters and compensating filters of the prior art and reduces the workload for the radiation technologists in treatment of the patient, while at the same time permits much improved precision in the two dimensional intensity distribution shaping of the resulting dose distribution in the patient. Furthermore, since my invention enables this beam shaping and intensity distribution control to be accomplished dynamically, it enables use of more effective treatment programs which would have been impractical in the prior art.

In conventional therapy, rectangular field shapes are formed by four motor driven jaws in the radiation head. Irregular field shapes for individual portals are then produced by mounting shadow blocks on a shadow tray between the jaws and the patient. The shadow blocks shield critical organs not invaded by the tumor. The radiation beam can be directed at the prescribed treatment volume from a single direction (single port therapy), from two or more directions (multi-port therapy), or the beam can be swept through an arc (arc or rotation therapy), all by rotating an isocentric gantry, for example. A cylindrical-shaped region of high dose is produced by a rectangular field in multi-port, arc or rotation therapy.

In multi-port therapy, the shadow blocks are changed for each beam angle. If the beam angle is not vertical, the shadow blocks must be locked to the shadow tray to avoid their falling off. Handling these blocks individually or on shadow trays is time-consuming. The shadow blocks are typically made by pouring a heavy metal into a pre-cut mold, which is also time-consuming. The shadow blocks can be heavy, difficult to handle, and dangerous if they fall on the patient or the radiotherapy personnel. In arc or rotation therapy, it is not practicable to change the shadow blocks continually or in small steps of beam angle. Also, this can require that the technologist go back into the shielded treatment room for each treatment field, a time-consuming process.

The usual treatment field shapes result in a three-dimensional treatment volume which includes segments of normal tissue, thereby limiting the dose that can be given to the tumor. The irradiation dose that can be delivered to a portion of an organ of normal tissue without serious damage can be increased if the size of that portion of the organ receiving such radiation dose can be reduced. Avoidance of serious damage to the organs surrounding and overlying the tumor determines the maximum dose that can be delivered to the tumor. Cure rates for many tumors are a steep function of the dose delivered to the tumor. Techniques are reportedly under development to make the treatment volume conform more closely to the shape of the tumor volume, thereby minimizing the product of volume and dose to normal tissue, with its attendant effects on the health of the patient. This other technique could possibly permit higher dose to tumors or can result in less damage to normal tissue. These techniques reportedly involve moving the x-ray jaws during treatment, scanning the x-ray beam or using multileaf collimators. Generally, in the prior art, multileaf equipment has not been capable of shaping internal regions of the field, e.g., islands and longitudinal peninsulas.

In a technique called dynamic therapy, one set of jaws is set to form a narrow (e.g., 4 cm) fan x-ray beam and the spread of the fan beam is varied by the second set of jaws to conform to the boundaries of the prescribed treatment volume as the beam is swept or stepped in angle around the patient and as the patient and associated table top are moved through the fan beam. A computer controls the movements of the table top in x, y and z, the gantry angle, the upper jaws during start and stop of the scan, the lower jaws throughout the scan, and the dose rate. The complexity is such that great care must be exercised in preparing for such treatments, which consumes considerable time.

A technique has also been proposed in which a narrow collimated lobe of x-rays is scanned over the treatment field, permitting production of irregular field shapes at selected beam angles. Because only a small fraction of the x-ray output is within the narrow lobe, the effective dose rate is low and the time to produce a portal field is hence long and multi-port treatment times are excessively long. Also, scanning individual fields is not readily applicable to arc and rotation therapy modes.

Machines have been built in which each of the lower pair of jaws is divided into a number (e.g., 5 to 32) of narrow bars called leaves. Each leaf may be about 8 cm thick (in the beam direction) to provide adequate attenuation of the x-ray beam (down to about 1%), about 0.5 to 1.5 cm wide and about 14 cm long physically (not SAD). Each leaf can be moved independently by a motor drive. This permits the production of irregularly shaped fields with stepped boundaries, thereby avoiding shadow blocks for many situations in portal therapy. The shape can be changed as the beam direction is swept in arc or rotation therapy. The disadvantage of this technique of replacing the lower jaws by a multiplicity of leaves is that each leaf is quite large and heavy, requiring a motor drive system which consumes considerable space. There is limited room in the radiation head for all these components so either sacrifices in performance are made (such as fewer leaves, limited field size) or the construction costs become large.

In a different technique, the conventional upper and lower pairs of jaws are retained and a set of leaves is mounted between the jaws and the patient. Each leaf moves in a plane, driven by a rotating cam or pushed by a form corresponding to the desired irregular field shape. In one early concept, each leaf was thick enough to attenuate the x-ray beam to the required level (to about 5% of unattenuated beam intensity), the ends and sides of the leaf forming a rectangular parallelpiped, hence the ends and sides were not aimed toward the x-ray source. In a recent concept, a multiplicity of small diameter rods forms a stack sufficiently thick to provide the required beam attenuation. Each rod can slide with respect to its neighbors. A form corresponding to the desired field shape boundary is used to push the assembly of rods so that their ends form a similar beam boundary. Since the rods are small in diameter, the radiation field boundary can be relatively smooth (very small steps) and tapered (focused) toward the source. However, varying the field shape as a function of beam angle without entering the treatment room can require a quite complex drive system because the large number of rods requires that they be driven enmasse instead of individually.

Wedge filters are pieces of metal which are tapered in one direction but of constant thickness in the orthogonal direction. They are used to produce a more uniform dose distribution in a treatment volume when it is irradiated from two directions which are less than 180° apart. And they are used at any gantry angle as a crude compensation for the variation in depth from the patient's surface to the plane at treatment depth. In both cases, only an approximate correction of dose distribution in the treatment volume is achieved. Typically, standard wedges are used, with wedge angles of 15°, 30°, 45° and 60°. Intermediate angles are achieved by using two exposures per field, one with wedge filter, one without. Since manual insertion and retraction of wedges is laborious, fixed angle (typically 60°) auto-retractable wedge filters have been developed. Essentially all wedged fields then require two exposures, one with the wedge filter, one without. This is a time-consuming process, especially in rotational therapy, since an extra gantry rotation is required.

Compensators, often termed compensation filters, are formed or assembled pieces of metal which are shaped to match the patient's demagnified anatomical shape so as to attenuate the x-ray beam by the amount that would have occurred if the patient thickness to depth of treatment plane were uniform. However, their use has been more limited because of the needs for custom shaping for each patient and manual insertion for each field.

Computed tomography (CT) images for treatment planning are typically obtained in successive planes which are normal to the patient axis. After transfer of these images, internal structures, target volume and patient surface can be outlined directly on the treatment planning computer display. However, in conventional radiotherapy, correction is required for divergence of the x-ray beam in the direction through the successive CT planes. This is a computation chore (beam's eye view) for the treatment planner and a mental visualization chore for the radiation therapist.

OBJECT OF THE INVENTION

An object of the invention is to provide an improved method of radiation treatment enabling more resolution and precision in treatment by more precisely enabling control of the radiation intensity distribution across the fan beam cross section.

A further object is to enable dynamic, real time changes in the cross section intensity distribution of the fan beam to provide more effective patient treatment.

A further object of the invention is to provide a new system or an accessory to conventional medical electron accelerators and to radiation treatment and like techniques to permit dynamic control of three-dimensional spatial distribution of radiation dose in a treatment volume of arbitrary external and internal shape employing a fan x-ray beam which can be delivered, for example, in the same parallel planes in the patient as the computed tomography (CT) imaging planes.

These objects of the invention and other objects, features and advantages to become apparent from the following descriptions.

SUMMARY OF THE INVENTION

A fan x-ray beam, such as is produced by employing a slit aperture in conjunction with an x-ray source, is established. This could be accomplished using the collimator jaws of a conventional medical linac to produce a rectangular slit field at normal treatment distance. A multileaf collimator (MLC) is positioned in the fan beam including a first set of leaves which can be individually moved into or out of the fan x-ray beam to block or pass individual radiation pixels. Continuous monitoring of alignment of the patient's anatomy with both inner and outer edges of the fan beam is obtained with a linear detector array retractably mounted on the opposite side of the patient from the x-ray source. Tapered extensions, added to a second opposite set of leaves of the MLC are variably positionable to attenuate the dose rate in individual radiation pixels of the fan x-ray beam. The patient scan is obtained by moving the patient perpendicularly to and through the fan x-ra field while the dose delivered in each radiation pixel is dynamically controlled. Normal tissue is protected by the positions of the first set of leaves of the MLC, which attenuate transmission to less than 5% of open field dose. Depth variations from the patient surface to the plane at treatment depth are compensated at each radiation pixel of the field by the positions of the tapered extensions of the second, opposite, set of leaves of the MLC, providing variable transmission from 50% to 100% of open field dose, for example. Reduced dose to critical organs such as the spinal cord can thereby be delivered in each treatment fraction.

To compensate for the fact that the treatment beam is now a fan shape, one can operate, for example, the klystron at higher than conventional RF power. The RF pulse length and the ratio of beam pulse length to RF pulse length are increased so that the beam duty cycle is increased. The purpose of this combination is to achieve preferred treatment times with the fan x-ray beam. For example, an open field dose of 300 cGy at depth of dose maximum (D-max) can be delivered to a 40×40 cm field in 240 seconds (4 minutes), with individual control of dose in each of 1600 1×1 cm radiation pixels.

The MLC can be constructed as an accessory to a standard conventional radiotherapy machine wherein by retraction of the compensator fingers to their storage positions on the MLC leaves, multileaf collimation of irregular fields is retained. By retracting the MLC leaves to their support frames, conventional x-ray therapy with the four jaws in the radiation head is retained using shadow blocks for irregular fields. Conventional electron therapy is also retained.

Because other modes of therapy may be retained, interlock sensors for excess electron beam current and collapsed electron beam lobe are installed in the radiation head. Since the MLC could be installed in the space normally occupied by the conventional wedge filter tray, an automatic retractable support tray system for opposed angle wedge filters and for custom compensators would be mounted inside the radiation head.

Advantages of the invention are:
1. Elimination of prior art shadow blocks, wedge filters, and conventional compensators. Wedge tilt in any direction relative to the field is obtainable without mechanical rotation.
2. One-to-one match of treatment geometry and CT slice images. Avoidance of beam's eye view treatment planning computation.
3. Increased depth dose for a given x-ray beam energy.
4. Reduced penumbra longitudinally at depths other than SAD with multiple ports.
5. Field sizes to 40 cm width and any length.
6. Scanning movement of patient table only longitudinally, eliminating need for lateral and vertical scanning movement of patient table by use of dynamic compensation and dynamic field shaping.
7. Continuous monitoring of alignment of patient's anatomy with treatment beam during every treatment, with image contrast sensitivity superior to conventional port films. When implemented as accessory, retains the capability of conventional electron therapy and of conventional x-ray therapy with collimator jaws and shadow blocks and with multileaf collimator.

These and further constructional and operational characteristics of the invention will be more evident from the detailed description given hereinafter with reference to the figures of the accompanying drawings which illustrate a current envisioned preferred embodiment and alternatives. Clearly, there are many other ways one might build the embodiments of the hardware to carry out the inventive method and these examples should not be considered as the only way considered to carry out the invention.

BRIEF DESCRIPTION OF THE DRAWINGS

FIG. 1 is a view from the x-ray source of multiple-leaf fields according to the invention.

FIG. 2 is an illustration of a complex target region for use of the invention, the region of cervix-pelvic nodes-para-aortic lymph nodes region based on: Chin, L. M., et al, "Int. J. Radiation Oncology, Biol., Phys" Vol. 7, pp 61-70.

FIG. 3 is a section of the target region in the patient mid-saggital section plane 3—3 of FIG. 2.

FIG. 4 is a section of the target region in the section plane 4—4 of FIG. 3.

FIG. 5 is a section of the target region in the section plane 5—5 of FIG. 3.

FIG. 9 is a view from the bottom of a fan x-ray beam flattening filter with inherent shielding.

FIG. 10 is a sectional view of the filter of FIG. 9 along the section line 10—10 in FIG. 9.

FIG. 11 is a sectional view of the filter of FIG. 9 along the section line 11—11 of FIG. 9.

FIG. 12 is an end view of the assembly showing attachment of collimator fingers to MLC leaves.

FIG. 13 is a side view of the assembly of FIG. 12 along the section line 13—13 of FIG. 12.

FIG. 14 is a section of an alternate embodiment of the MLC leaves shown in FIG. 12.

FIG. 15 is a section of a second alternate embodiment of the MLC leaves shown in FIG. 12.

FIG. 23 shows a forty-leaf collimator showing support motor drive with compensator fingers attached as viewed from isocenter.

FIG. 25 is a sectional view of the collimator of FIG. 23 along the section line 25—25.

FIG. 26 is a sectional view of the collimator of FIG. 23 along the section line 26—26 to show the curved end tapered MLC leaves.

FIG. 27 is a sectional view of the collimator of FIGS. 23-26 along section line 27—27, showing frames, lead screws, ball bearings and support rods.

FIG. 28 is a sectional view of the collimator of FIGS. 23-27 along section line 28—28.

FIG. 32 shows control and monitoring electronics for MLC and compensator fingers.

LEXICON

Figures 1A, 1B:
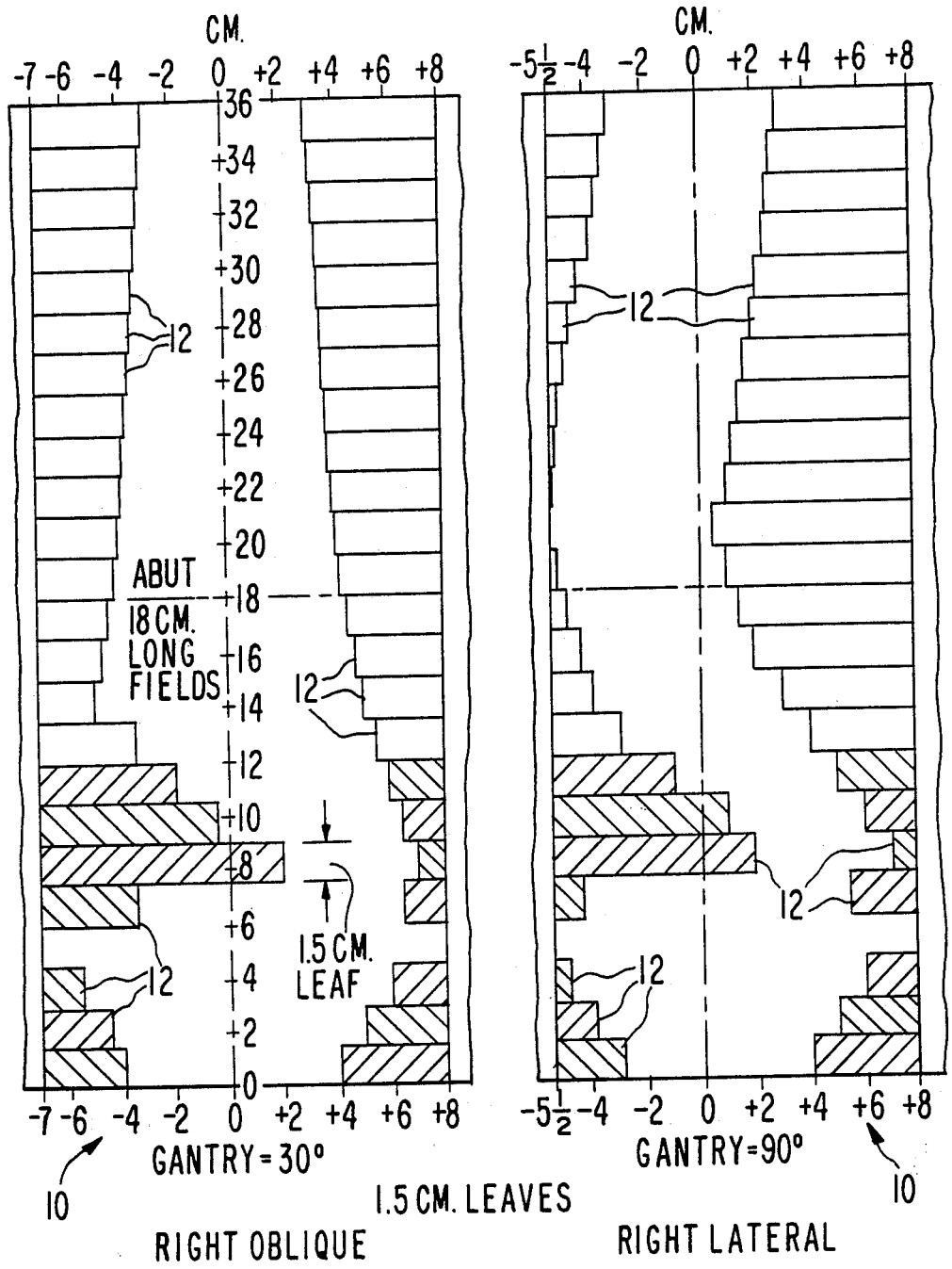
FIG. 1a shows the leaves in the configuration for a right oblique treatment of the region of FIGS. 2-5.
FIG. 1b shows the leaves in the configuration for a right lateral treatment of the region of FIGS. 2-5.

The following is a listing of terms, abbreviations, units, and definitions used throughout this specification.

cGy: centiGray, $10^{-2}$ Joules per kilogram of absorbed dose, a unit of mean energy imparted by ionizing radiation to matter.

compensator filter: device which modifies the distribution of absorbed dose over the radiation field.

depth dose: absorbed dose at a specified depth beneath the entrance surface of the irradiated object.

D-max: depth of maximum absorbed dose.

dynamic changing with time in accord with a radiation plan as the radiation dose progresses.

flattening filter: device which homogenizes the absorbed dose over the radiation field.

imaging pixel: rectangular elements which together add to form an image.

isocenter: the position around which the radiation x-ray therapy source moves to achieve optimum treatment of a tumor in a patient.

MeV: million electron-volts.

MLC: multileaf collimator.

penumbra: fringe at edges of the radiation field, where the radiation intensity falls off rapidly with distance from the full intensity region of the field.

radiation pixel: rectangular elements of radiation which together add to form the radiation field.

SAD: source-axis distance, the distance from the x-ray source to the isocenter.

SSD: source-skin distance, the distance from the x-ray source to the skin of the patient.

tomography: radiography of layers (slices) within the patient.

Other standard terminology is defined in *Medical Radiology—Terminology*, Pub.788, International Electrotechnical Commission, Geneva, Switzerland, 1984.

Glossary

The following is a glossary of elements and structural members as referenced and employed in the present invention.

10—collimator
11—flat cylinder
12—leaves
14, 16—multileaf half assemblies
18, 20—leaf support frames
22, 23—lower jaws
24—electrical drive motor for half frame
25—threaded shaft
26—rod
27—threaded bushing
28—upper sub-leaves
29—lower sub-leaves
30, 32—rods
34, 36—bushings
38—threaded shaft
40—threaded hole
42—flexible cable
44—motor
46, 48—spur gears
50, 52—subframes
54—correction motor
56—chain
58—sprocket
60—rods
62—upper plate
64—side wall
66—lower plate
68—lip
70—jaw frame
72—bearing
80—flattening filter assembly
82—slit aperture
84—flattening filter piece
86—cylindrical tungsten shield piece
88—aluminum mounting plate
90—MLC leaves with multiple notch
92—compensator fingers
94—slide bar
96—mating slot
98—support rod
100—lead screw
102—detent
104—notch in the MLC leaf
106—ridge in the MLC leaf
108—alternate MLC leaf with simple notch
110—second alternate MLC leaf
112—linear array of detectors
114—gantry
116—patient treatment table
118—MLC housing
120—fan beam
122—detector crystals
124—shielding strips
126—photodetectors
128—lead strips
130—collimator slit
132—electronics
134—telescoping support
136—analog multiplexer
138—preamplifier
140—integrator
142—sample and hold circuit
144—integrator
146—A/D convertor
148—computer memory
150—clock and timing controls
152—control logic
154—video monitor
156—leaves 158—drive system
160—support frame
162—motors
164—threaded shafts
166—collimator jaws
168—TV camera
170—lens
172—mirror
174—toroid
200—reflective surface
202—flange
204—fiber optics for light
206—fiber optics for detector
208—first foil
210—second foil
212—button
214—foil holder
216—spring
218—bellows
220—lip on foil holder
222—pinch off
224,226—trays
230—upper jaws
231—drive apparatus for upper jaws
232—ionization chamber
234—x-ray target
236—electron window
238—carousel for filter and scatterer
240—lower jaws
242,244—wedge filters
246,248—support bars
250,252—lead screws
254—motors
256—lead shielding

DETAILED DESCRIPTION OF THE PREFERRED EMBODIMENTS

Referring now to the drawings wherein reference numerals are used to designate parts throughout the various figures thereof, there is shown in FIG. 1 an example of multileaf field shapes of the collimator 10 mounted in a flat cylinder 11 for a complex shaped clinical site, the region of cervix-pelvic nodes-para aortic nodes, as illustrated in FIG. 2. In this example, the field is 36 cm long. Its irregular width is defined by 24 pairs of leaves 12, each producing a 1.5 cm strip shadow in the radiation field at SAD (source-axis distance). The fields are presented for only two gantry angles but they illustrate the range of field shape variation during essentially full gantry rotation.

FIG. 1 is drawn assuming that both upper and lower conventional jaws are used to define the field rectangular limits (36 cm long, 15 cm wide at 30° gantry angle, 13.5 cm wide at 90° gantry angle) and that the multileaf system simply provides the extra shadow blocking required within the rectangle. This permits shallow leaves 12 of 4.5 cm (1.77 inch) thickness tungsten (18.2 g/cm$^3$) for 5% transmission, the usual shielding criterion for shadow blocks, instead of 7 cm or more thickness tungsten for 1% transmission, the usual criterion for jaws. The maximum extension of any leaf into the field in FIG. 1 is only 9 cm at SAD and only 2 cm beyond centerline. Assuming a more extreme case of 5 cm extension beyond centerline from a field edge 7 cm from field center; 2 cm beyond center for a 20 cm wide field; and allowing for about 1 cm jaw overlap, the leaves would need to be only 13 cm long projected to SAD, about 6.84 cm (2.7 inches) actual length.

Figure 7:
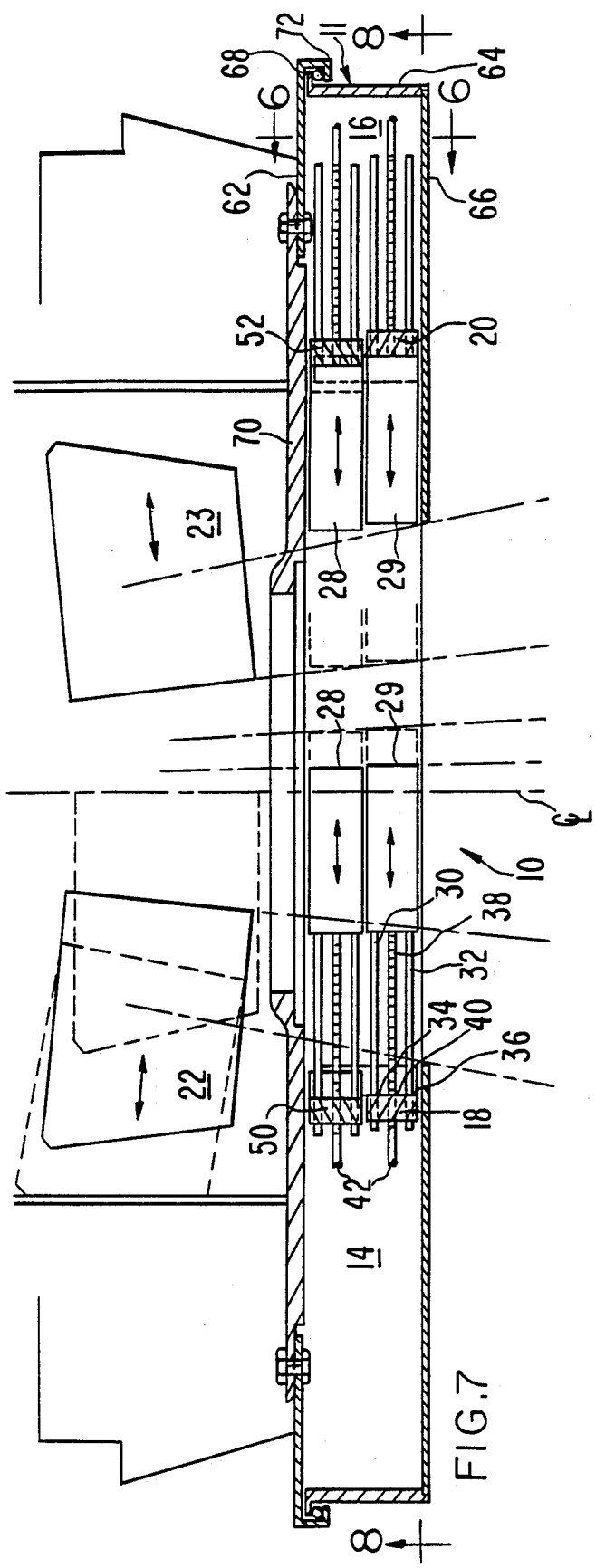
FIG. 7 is a sectional view of the collimator according to the invention as shown in the section plane 7—7 of FIG. 8.
Figure 6:
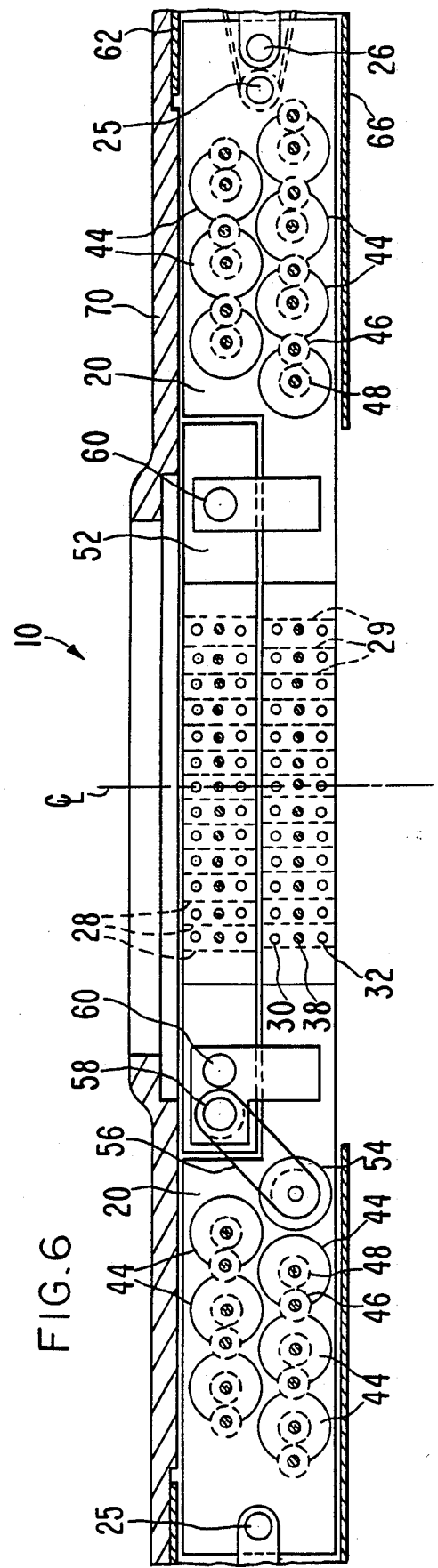
FIG. 6 is a sectional view of the collimator according to the invention as shown in the section plane 6—6 of FIG. 7.
Figure 8:
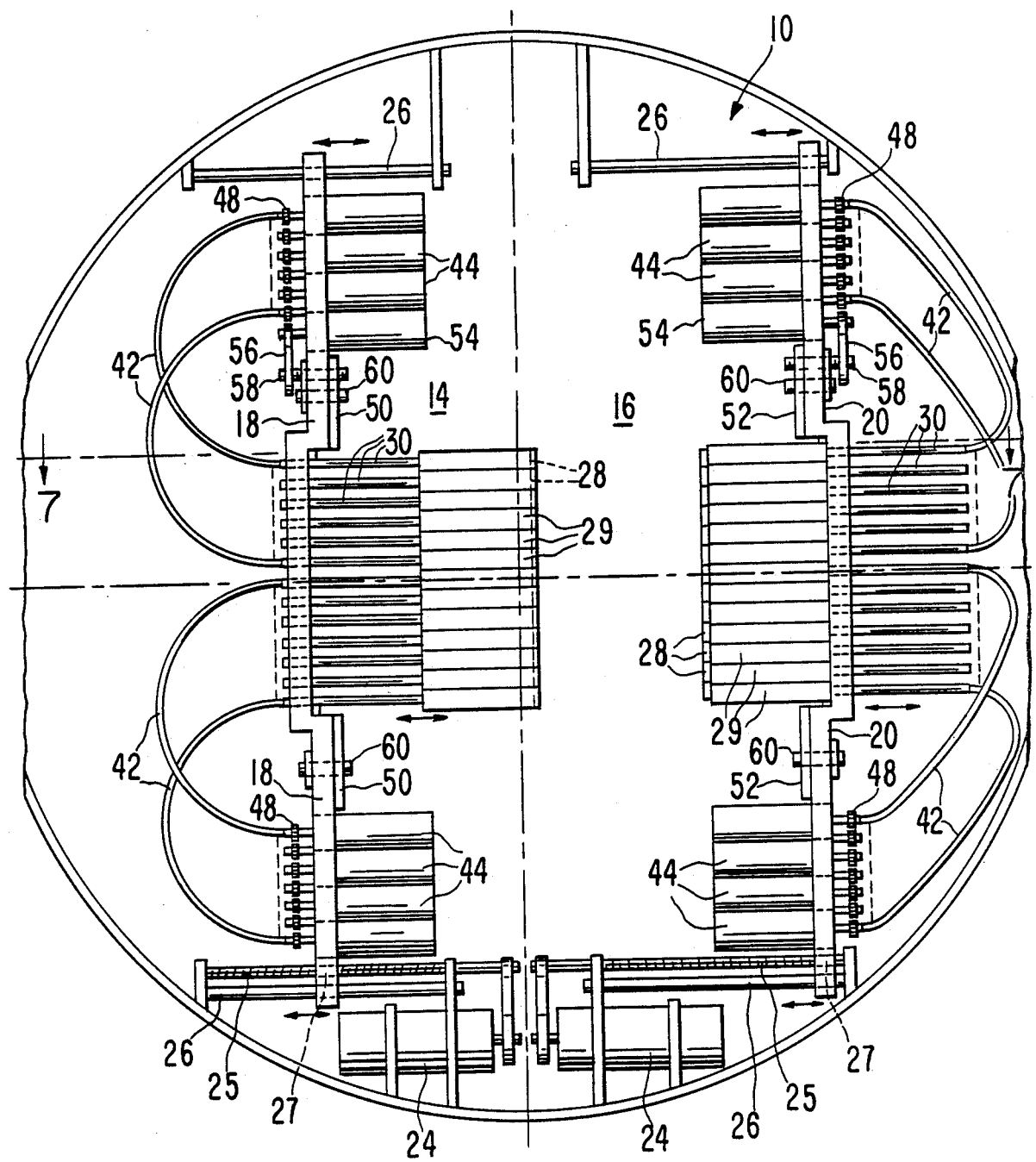
FIG. 8 is a view of the collimator of the invention as seen from the patient treatment region looking toward the x-ray source.

About 95% of all treatment fields fit within a 20 cm×20 cm square. Assuming the projected width of each leaf is 1.5 cm, 13 leaves would cover a 19.5 cm field length. FIGS. 6–8 show such a design. The leaves 12 are mounted in the space presently occupied by the wedge mount of one type of conventional radiotherapy machine, at 52.6 cm from the x-ray source. Each leaf 12 actual dimension is on 0.786 cm (0.31 inch) pitch, is 4.5 cm (1.77 inch) deep, 7.0 cm (2.75 inches) long, and weighs 0.45 kg (0.99 pound) of 18.2 g/cm$^3$ density tungsten. The total of 13 leaf pairs weighs 11.7 kg (25.7 pounds). If a light weight or detachable drive is used, it is conceivable that the multileaf assembly can be removed by radiation technologists, one-half (13 pounds, plus drive) at a time. The total weight of all leaves is only 21% the weight of the conventional lower jaws. Each gear motor weighs about ½ pound.

Each multileaf half assembly 14, 16 is mounted on a leaf support frame 18, 20 which can be moved in concert with its corresponding lower jaw 22, 23, either by lever connection to the jaw or by chain or other connection to the drive for that jaw or preferably by independent electrical drive 24 for each half frame. Each independent electrical drive 24 is mounted to the cylinder 11 and is coupled by gears, belts or chains to a threaded shaft 25 which drives a leaf support frame sliding on rod 26 and attached to a threaded bushing 27. Thus, the maximum distance any leaf must travel is only the maximum distance it can project into the rectangular field defined by the upper and lower jaws; in this example, 6.6 cm (2.6 inches) actual travel distance relative to the frame.

If the lower jaws 22, 23 are symmetrically driven, one multileaf half assembly 14, 16 can be driven as a monoblock to provide dynamic wedge fields up to 12 cm. If the lower jaws are driven independently but are not enlarged in width and travel only up to field center, the multileaf half assembly can be driven as a monoblock to travel 12 cm beyond field center, thereby providing dynamic wedge fields up to 24 cm. Thus, independent jaws can be smaller in combination with the multileaf system than if the independent jaws themselves must be driven past field center and their tails still shield the primary collimator opening.

It is desirable to use straight leaves and to have them travel in a straight line. This minimizes the depth (in SAD direction) of the multileaf assembly and simplifies mounting and driving the leaves. It avoids curved tracks and in adapting to existing radiotherapy machines it avoids penetrating into the frame that supports the existing collimator. To achieve approximate alignment of the ends of the leaves with a line from the x-ray target over the full leaf travel, each leaf 12 is actually comprised of two sub-leaves 28, 29, one above the other. Hereinafter upper is taken as meaning closer to the radiation source and lower to mean further from the radiation source. The lower sub-leaf 29 travels slightly faster than the upper sub-leaf 28, so that their ends are staggered to match the angle from the x-ray target. The lower sub-leaf 29 is also slightly wider (2.2 mm in this example) than the upper sub-leaf 28, so that their sides are staggered to match the angle from the x-ray target in the direction at 90° to the leaf travel. The contribution to penumbra due to staggering instead of tapering the leaves is 2.5 mm maximum (80% to 20% dose), at 20 cm field. This will increase total penumbra from a 6 mm to $(6.2^2+2.5^2)^{0.5} = 6.5$ mm.

Each sub-leaf is supported by two rods 30, 32 (e.g., ⅛ inch diameter) which pass through two bushings 34, 36 (e.g., ¼ inch outside diameter) in a frame 18, 20, and a threaded shaft 38 (e.g., ⅛ inch diameter) which passes through a threaded hole 40 in the frame. The individual sub-leaves 28, 29 have sufficient clearance (e.g., 0.2 mm) so that they do not rub on each other, hence avoiding extra friction and the need for radiation resistant dry lubricant (e.g., molybdenum disulphide) in the x-ray beam. Each lower sub-leaf 29 is motor-driven back and forth on micro-processor (not shown) command via the threaded shaft 38, driven through flexible cable 42 from a gear motor 44. The weight of each pair of sub-leaves 28, 29 is about 1 pound, and this weight would need to be supported at 90° gantry angle. It would be desirable to be able to change any leaf position by 5 cm (SAD) in 5° of gantry rotation (0.83 seconds). Adding gear friction, etc., 5 pounds force over 2.7 cm actual travel in 0.8 seconds corresponds to 6.5 inch pounds per second or $10^{-3}$ horsepower, permitting use of a miniature gear motor 44 for each pair of sub-leaves 28, 29, total of 26 such motors for 13 sub-leaf pairs, 13 motors per side. These can be arrayed within the vertical space of the conventional wedge mount. The upper sub-leaf 28 of each split leaf is driven at a slightly lower speed via two spur gears 46, 48 at the gear motor. A rotation counter (not shown) can be installed in the flexible cable drive to each sub-leaf, or to just the upper or lower set of sub-leaves. Each turn of the cable to a ⅛ inch diameter 12:1 lead screw corresponds to about 0.5 mm change in field edge at SAD. A plus or minus signal for plus or minus one rotation will be sent to a summing circuit and the position of the field edge of each leaf will be displaced digitally and on a CRT. The power to the motor drive will be stopped when this display corresponded to the value of field edge previously set for that leaf at that gantry angle.

The upper sub-leaves 28 are supported on subframes 50, 52 the lower sub-leaves 29 on frames 18, 20. Both subframes 50, 52 are driven from the existing lower jaw drive. Alternatively, motors 54 can be added to drive each frame under control signals independent of the jaw drives. The upper subframe 50 is driven slightly slower than the lower subframe 52 by a correction motor 54, chain 56 and sprocket 58, such that upper subframe 50 slides on rods 60 and such that the frame ends are staggered to match the jaw face slope. The stagger of the sub-leaf ends is then correct for all jaw positions.

FIG. 7 is a drawing showing the planar multileaf system in the vertical space normally occupied by the wedge mount. The left side of the collimator 10 shows the lower jaw 22 set for a 20 cm conventional field, with leaves penetrating to 2 cm beyond field axis. The right side of the collimator shows the lower jaw 23 set for a 40 cm conventional field, with the leaves fully withdrawn. This establishes the required diameter of the multileaf system housing. The set of 13 split leaves on the right side is driven by a set of 13 gear motors 44, 7 motors being on one side, 6 motors on the other side of the set of leaves. This provides room for the drive cables 42, one for each sub-leaf driven directly by a gear motor 44, the other sub-leaf through a pair of gears 46, 48 at the gear motor. The 13 motors 44 are mounted on the leaf support frame 20 which is driven by a lead screw via a chain from the lower jaw drive system or preferably by a motor 24.

Since the depth of the leaves is so small for 5% transmission in tungsten, it may be clinically acceptable to use single leaves of tapered cross-section instead of staggered split leaves. The leaf penumbra (20% to 80%) at SAD will be 5 mm maximum (20 cm field), which will increase conventional penumbra from 6 mm to $(6.2 + 5.2)^{0.5} = 8$ mm. Avoiding the staggering will reduce the complexity and cost of the mechanical part of the multileaf system, but the number of motors and the microprocessor control will remain the same.

The flat cylinder 11 containing the multileaf collimator 10 can be mounted rotatably on the radiation head. The flat cylinder 11 includes an upper plate 62, a side wall 64 and a lower plate 66. The side wall 64 has a lip 68. The upper plate 62 is fastened to the jaw frame 70, extends beyond the side wall and supports a multiplicity of bearings 72 which support the side wall 64 on the lip 68 and permit rotation of the collimator. A single lock may be provided to hold a rotational position or the friction of the bearings can be increased to provide holding means. This will permit setting the jaws for a rectangular field at one angle relative to gantry axis (and patient) and the multileaf system set an another angle, corresponding more closely to an anatomical edge of interest, such as the spinal cord. This will result in a less stepped edge to the multileaf field.

The jaws are tilted as they are opened in order to provide an edge surface parallel to the path of the radiation. In an alternate embodiment, one layer of leaves can be used with the leaf sides in planes containing the radiation source and with the leaf end curved so as to be always tangent to a plane containing the radiation source, thereby minimizing penumbra. This is shown in FIGS. 12-13 and 21-28.

Further alternate embodiments described hereinafter can be used with a fan beam of x-ray radiation.

Figure 16:
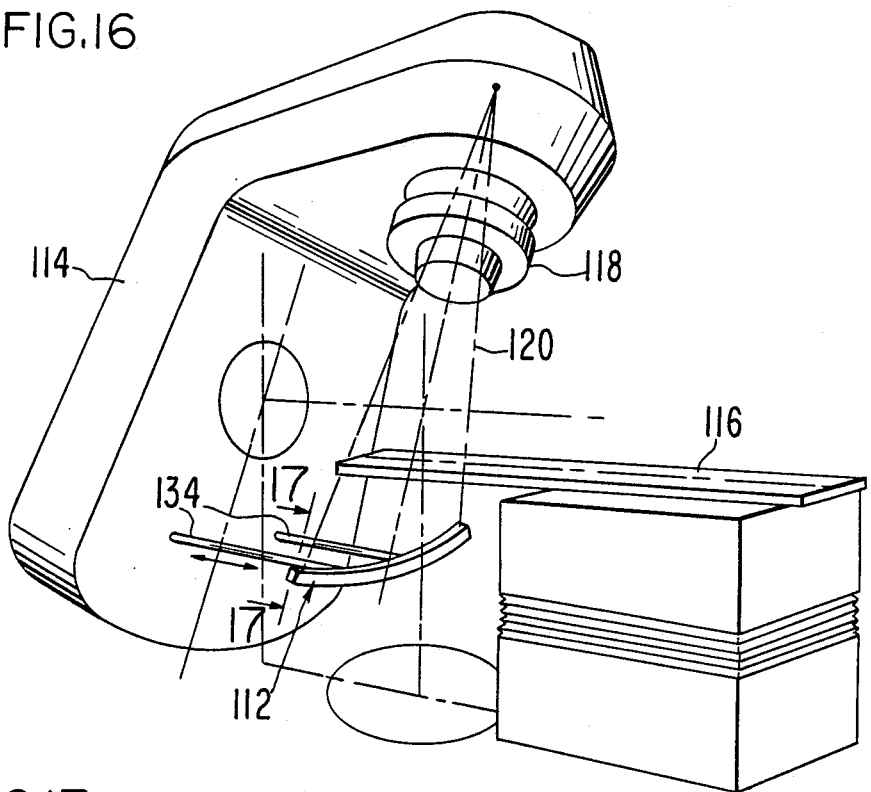
FIG. 16 shows a gantry mounted linear array detector.
Figure 24:
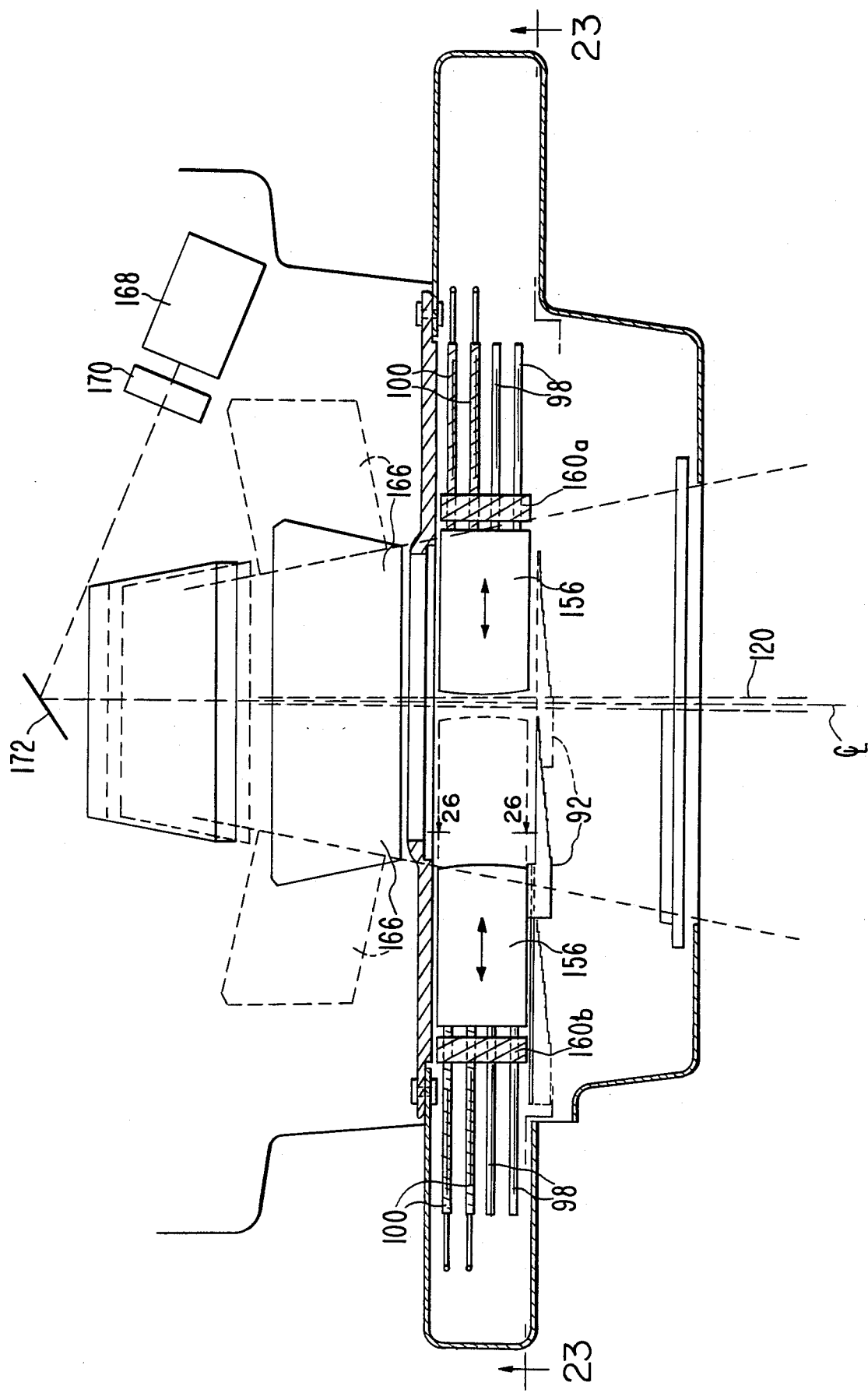
FIG. 24 is a sectional view of the collimator of FIG. 23 along the section line 24—24 from the side with compensator fingers attached.

In conventional radiotherapy, an x-ray energy of approximately 6 to 10 MeV is preferred for the majority of treatment fields, especially for head and neck tumors and for the lymph system extending to near the patient surface; approximately 18 to 25 MeV is preferred for the remaining fraction of fields for more deeply seated tumors such as in the abdomen and pelvis. The depth to D-max and depth dose at 10 cm depth for conventional 10×10 cm field are approximately 1.5 cm and 67% for 6 MeV x-ray beam; 3.3 cm and 79% for 18 MeV x-ray beam, all for phantom surface at 100 cm from the source. With a fan x-ray beam as shown in FIGS. 16 and 24 and with the patient or test object moved through the fan to produce a field, the radiation diverges in only one dimension instead of the conventional two dimensions. The depth dose in the field at 10 cm depth with the fan x-ray beam increases to 72% at 6 MeV, 84% at 18 MeV, corresponding respectively to the depth dose of conventional 9.5 MeV and 25 MeV x-ray beams.

Take as an example, moving the patient through the fan to produce 40 cm long fields with a 1 cm slit x-ray fan at each of 6 gantry angles in a total of 5 minutes, 1 minute total for gantry rotation and 4 minutes total for field scans. The scan speed for each of the 6 fields will be 1 cm per second. The dose at D-max in each field at 3000 cGy/minute (50 cGy/ second) will be 50 cGy. Assuming 67% depth dose at the tumor depth, the tumor dose will be 33 cGy per field, 200 cGy for the 6 fields, which is a typical tumor dose per daily treatment in conventional radiotherapy. The 67% depth dose value will correspond to about 12 cm depth of tissue with 6 MeV fan x-ray beam, about 18 cm depth of tissue with 18 MeV fan x-ray beam. The insertion of compensator fingers for tissue compensation will not require increased exposure time in most cases because they will be inserted only in regions of reduced anatomical depth from the patient's surface to the plane at tumor depth. Similarly, a 20 cm long field at each of 6 gantry angles can be scanned at 0.5 cm per second in a total of 5 minutes with 0.5 cm slit fan x-ray beam for improved spatial resolution or in 3 minutes with 1 cm slit fan x-ray beam, allowing 1 minute for gantry rotation in each case. Using the compensator fingers to produce a wedged field for dual port therapy at other than 180° will reduce the dose rate but wedge fields are typically less than 15 cm so again the total scan time even at 0.5 cm per second is acceptable.

Inner boundaries (islands, longitudinal peninsulas) of all fields and outer boundaries of irregular fields will be defined by timing of insertion of individual leaves of the first set of leaves of the multileaf collimator. With 1 cm leaf pitch at SAD, a finer increment in position of the 50% isodose line at lateral edges for example, can be obtained by partial insertion of a leaf into the 1 cm strip fan x-ray beam. This interpolation process can be especially useful in more precise definition of inner boundaries (islands and longitudinal peninsulas) which cannot be shaped by the collimator jaws which are orthogonal to the fan. One set of collimator jaws, which can move symmetrically, will form the 0.5 cm or 1 cm slit fan x-ray beam. If the orthogonal set of collimator jaws moves independently, they can be used to define the outer boundary of the irregular field more precisely than in the 1 cm full or interpolated lateral steps of the multileaf collimator. It will be possible to move the patient table only longitudinally, with the fan boundaries being varied to match the varying outer boundary of the treatment volume and with the varying depth to the center of the treatment volume in each slice being compensated dynamically by varying the insertion of the compensator fingers.

Consider the hypothetical situation where a multileaf collimator (MLC) has been installed in a machine inside the radiation head in the position of the lower set of collimator jaws, replacing them. Since a lower set of collimator jaws does not exist, the MLC must be used to form the fan beam. Hence, motion of such a MLC is not available for driving dynamic compensator leaves, so they will have to be mounted and driven separately from the in-the-head MLC.

The flattening filter will be designed to produce a flat isodose curve at a chosen depth, such as 10 cm at 6 MeV, 15 cm at 18 MeV. Isodose curves at shallower and greater depths will be slightly concave or convex, respectively, because of scatter in the patient and because of spectral energy variations with angle. The latter will be less with a fan beam than with a conventional cone x-ray beam. The actual depth of the flattest isodose curve can be varied from that produced by the flattening filter by appropriate setting of the compensator fingers.

The unflattened central axis dose rate at 100 cm is 12.5 cGy/minute per microampere of electron beam current on a thick tungsten x-ray target at 6 MeV; 160 cGy/minute at 18 MeV. The angle of a 40 cm fan at 100 cm SAD is ±11.31°. The x-ray lobe intensity at this angle is 60% of central axis dose rate at 6 MeV; 27% at 18 MeV. The required average electron beam current and power at the x-ray target for 3000 cGy/minute at 100 cm SAD at the ±11.21° fan angles, unattenuated, are 400 microamperes and 2.40 kW at 6 MeV; 70 microamperes and 1.26 kW at 18 MeV. At these beam power levels, it may be necessary to shape the tungsten button of the x-ray target conically in order to provide additional heat conductivity.

The transmission of the bend magnet system from accelerator guide output to x-ray target is about 75%. Thus, an average beam current and power from the accelerator guide is required of 533 microamperes, 3.20 kW at 6 MeV; 93 microamperes, 1.68 kW at 18 MeV. Medical accelerator klystron and modulator ratings can be upgraded from conventional operation at 2.75 MW or 5.5 MW pulse, 300 or 150 pulses per second, respectively, at 4.5 microsecond RF pulse length and 3.71 kW average RF power to 2.75 MW or 5.5 MW pulse, 360 or 180 pulses per second, respectively, at 10 microseconds RF pulse length, and 9.9 KW RF power. This permits increase of the accelerator beam pulse length from 3.5 microseconds to 9 microseconds and increase of the beam duty cycle by a factor of 3.1.

Assume a 1.5 meter long, 90 megohm/meter shunt impedance standing wave accelerator guide with microwave energy switch at 0.5 meter from injection, set to obtain 6 MeV in this 0.5 meter length in either a 6 MeV or 18 MeV mode. The required pulse power loss in the accelerator guide walls is:

$$P = V^2/(r \cdot L) = (6)^2/(90 \times 0.5) = 0.8 \text{ MW at 6 MeV}.$$
$$= (18)^2/(90 \times 1.5) = 2.4 \text{ MW at 18 MeV}.$$

Assume a pulse rate of 360 pps in 6 MeV mode, 180 pps in 18 MeV mode, 10 microsecond Rf pulse length, 9 microsecond beam pulse length. Assume 80% of the klystron Rf pulse power can be usefully converted to accelerator guide loss and beam power. The following set of operating parameters can be obtained:

| Beam energy mode | 6 MeV | 18 MeV |
|---|---|---|
| Klystron pulse power | 2.75 | 5.5 MW |
| RF pulse length | 10 | 1.0 ms |
| RF pulse rate | 360 | 180 pps |
| Useful RF pulse power | 2.2 | 4.4 MW |
| Accelerator guide pulse power | 0.8 | 2.4 MW |
| Beam pulse power (out of guide) | 1.4 | 2.0 MW |
| Beam pulse length | 9 | 9 ms |
| Beam duty cycle | 3.24 | $1.62 \times 10^{-3}$ |
| Beam average power (out of guide) | 4.54 | 3.24 kW |
| Beam pulse current | 233 | 111 mA |
| Beam average power at x-ray target | 3.4 | 2.43 kW |
| Required Power at x-ray target for 3000 cGy/min | 2.4 | 1.26 kW |

IEC Standard 601-2-1 requires shielding of the x-rays to 0.6% of central axis dose within a 40×40 cm maximum field size; to an average of 0.1% over the remainder of the circle of 2 meters radius in the patient plane at 100 cm from the x-ray target; and to 0.5 over the remainder of the envelope at 100 cm from the path of the accelerator electron beam. Because the average electron beam power at the x-ray target has been increased, the attenuation of the radiation head shielding should be increased by a factor of 4, corresponding to 4 cm of additional lead.

With one set of collimator jaws nearly closed to form the slit fan x-ray beam, and with one set of leaves of the multileaf collimator positioned adjacent or protruding into this fan beam, additional shielding of a 40×40 cm area is required only on the opposite side of the fan where the MLC leaves are partially or wholly retracted. This can be done by inserting a 0.5 cm thick tungsten or 0.8 cm thick lead block in the shadow tray region when the fan beam is used. The block area at 64 cm from the source will be approximately 13×26 cm and will have a total weight of 3 kg. The remainder of the factor of 23 shielding of this area is provided by 3.5 cm thickness of tungsten at the x-ray fan beam flattening filter assembly 80, shown in FIGS. 9–11, which has a slit aperture 82 about 3 mm wide in a 6.6 cm diameter cylinder. The filter assembly is formed of a tungsten flattening filter piece 84, located below the slot 82. The slit 82 is formed in a cylindrical tungsten shield piece 86. The flattening filter piece 84 and the tungsten shield piece 86 are mounted on an aluminum mounting plate 88.

The MLC leaves 90, shown in FIGS. 12–13, are made of tungsten to minimize their height as well as to minimize radioactivity which might otherwise be induced, especially by the 18 MeV x-ray beam. The compensator fingers 92 are also made of tungsten to minimize induced radioactivity by the x-ray beam. The slide bar 94 which provides for support and sliding of the compensator fingers 92 with respect to the MLC leaves 90 is made of molybdenum, to reduce sliding friction and to avoid excessive induced radioactivity. The slide bar 94 fits into a mating slot 96 in each compensator finger 92. Each MLC leaf 90 is moved on a support rod 98, and is propelled through a lead screw 100. Each compensator finger 92 includes within it a pair of spring-loaded detents 102 to hold it in place to the slide bar 94. Each MLC leaf 90 has multiple notches 104 on one side and ridges 106 on the opposite side to provide for radiation shielding of the gap between adjacent leaves. The width of the ridges 106 is less than the width of the notches 104 and there is also a small gap between leaves to prevent sliding friction of touching surfaces.

In one alternate embodiment of the MLC leaves 108 shown in section in FIG. 14, a single ridge on one side and a single notch on the opposite side are employed. In another alternate embodiment of the MLC leaves 110 shown in section in FIG. 15, a complementary pair of offsetting shoulders are used to provide the gap radiation shielding. These various embodiments of the MLC leaves can be used to work out the placements of support rods 98, lead screws 100 and the drive system for different dimensions, and none has any inherent advantage for all sizes of parts.

Figure 17:
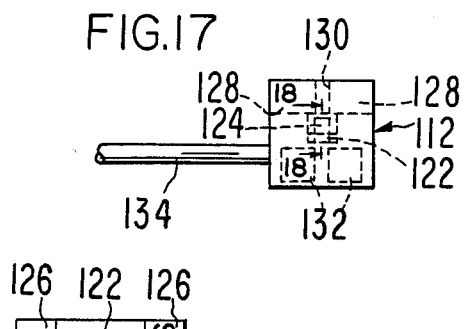
FIG. 17 is a sectional view of the detector array shown in FIG. 16 along the section line 17—17.
Figure 18:
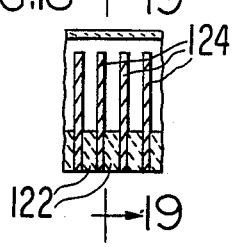
FIG. 18 is a sectional view of the array shown in FIG. 17 along the section line 18—18.
Figure 19:
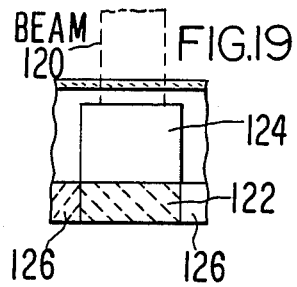
FIG. 19 is a sectional view of the array shown in FIG. 18 along the section line 19—19.

At 6MeV x-ray energy there are about $10^9$ photon/cm$^2$ per cGy. At 3000 cGy/minute, 50 cGy/second, after attenuation through the patient there are about $10^{10}$ photons/cm$^2$ per second in the fan beam, with mean photon energy of about 2 MeV. Their attenuation in 1 cm thickness of high density crystal detector material is about 10%. In FIG. 16, a 128 element linear array 112 is shown in perspective mounted on the gantry 114 with the patient treatment table 116, the MLC housing 118, and the fan beam 120. Further views of the array 112 are shown in FIGS. 17–19.

The array 112 can be made of 0.3 cm thick 1 cm deep scintillator strips of bismuth germanate or cadmium tungstate crystals 122 on 0.5 cm centers over the 64 cm fan x-ray beam arc dimension at 160 cm from the x-ray source (40 cm SAD). Interleaved with the crystals 122 there are 0.2 tungsten or lead shielding strips 124. The crystals 122 are optically coupled to an array of 128 photodetectors 126 which will detect about $10^6$ MeV x-ray beam photons per 1/30 second. A cross section of the array is shown in FIG. 18, to show two strips of lead 128 about 2.5 cm thick used to shield the array 112 from x-rays scattered in the patient. A gap between the lead strips 128 forms a slit collimator 130 above the crystals 122. Signal processing electronics 132 is placed below and on either side of the crystals 122. This system provides adequate quantum statistics for real time display of patient anatomy during each field scan, with useful contrast sensitivity. The array 112 is mounted on a telescoping support 134 attached to the gantry 114.

Figure 20:
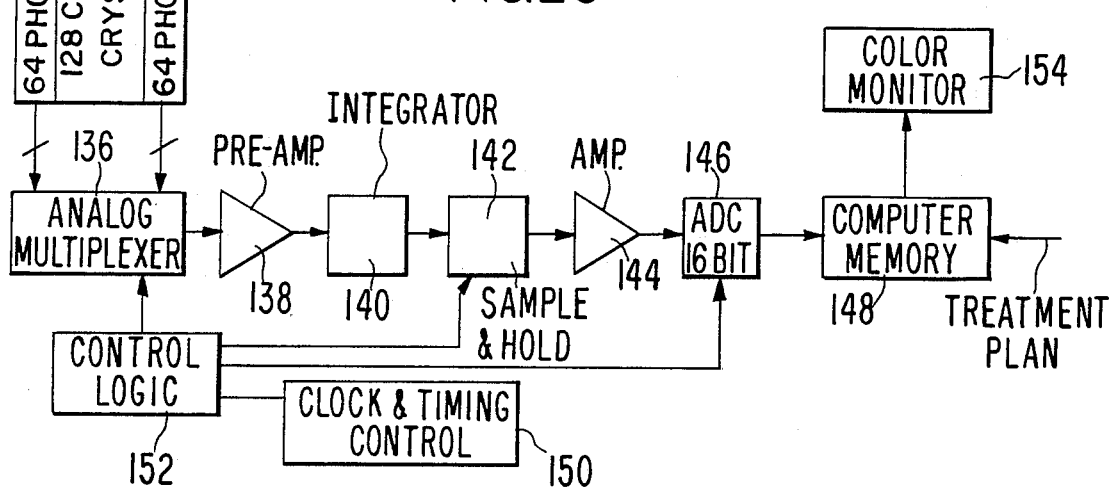
FIG. 20 is a block diagram of the electronics system for the linear array detector of FIGS. 16-19.

FIG. 20 shows a block diagram of the electronics needed for such a system. An image can be built up line-by-line on a refreshed CRT screen as the patient table is moved longitudinally through the fan x-ray beam, producing a "Scout" projection view similar to that obtained with CT scanners, but at 6 MeV instead of about 120 kV x-ray energy for initial localization and at either 6 or 18 MeV during treatment. Cross-talk between crystals can be unfolded by convolution techniques. The contrast sensitivity of the image with the fan x-ray beam will be superior to what will have been obtained with a conventional full field x-ray beam because the Compton scatter photons produced in the patient by the fan x-ray beam will largely miss the detector. The digital format of the real time image data also facilitates computerized image enhancement and real time comparison with patient anatomical outlines from the treatment plan. The detector can be oscillated laterally by 0.25 cm at about 4 cycles per second to provide interlaced image pixels for higher lateral spatial resolution.

The output of each photodiode 126, as shown in FIG. 20, is fed through an analog multiplexer 136 to a FET pre-amplifier 138, integrator 140, sample and hold circuit 142, analog amplifier 144, and analog-to-digital convertor 146 to a computer memory 148. The multiplexer interrogates each of the 128 integrators once each 1/30 second being stepped by the clock and timing control 150 and control logic 152 circuits. The detected amplitudes which have been stored in computer memory 148 are used to modulate the intensity of a CRT beam as it scans and builds a TV raster image and to refresh the image of a monitor 154.

Figure 21:
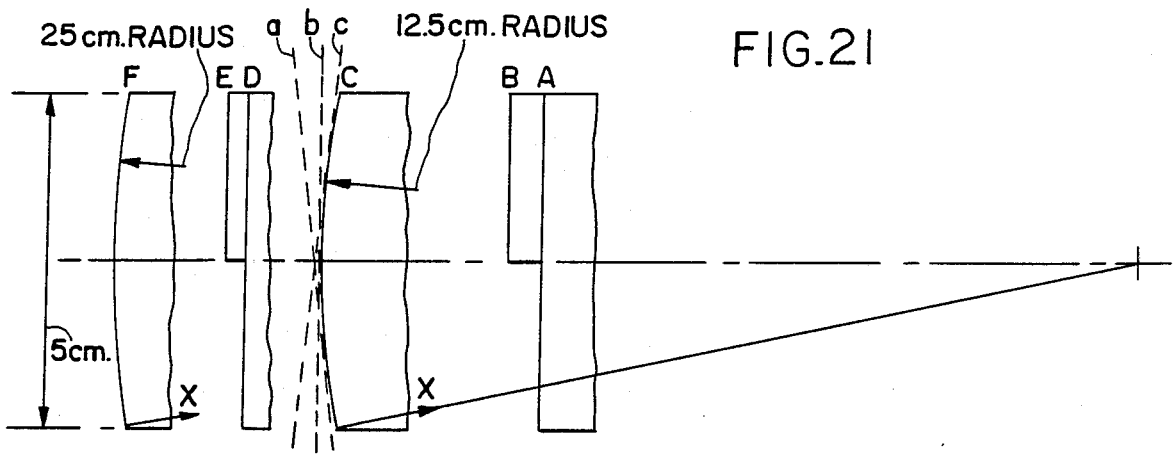
FIG. 21 is a diagram defining the parameters for calculating the multileaf penumbra for various shaped leaf ends.
Figure 22:
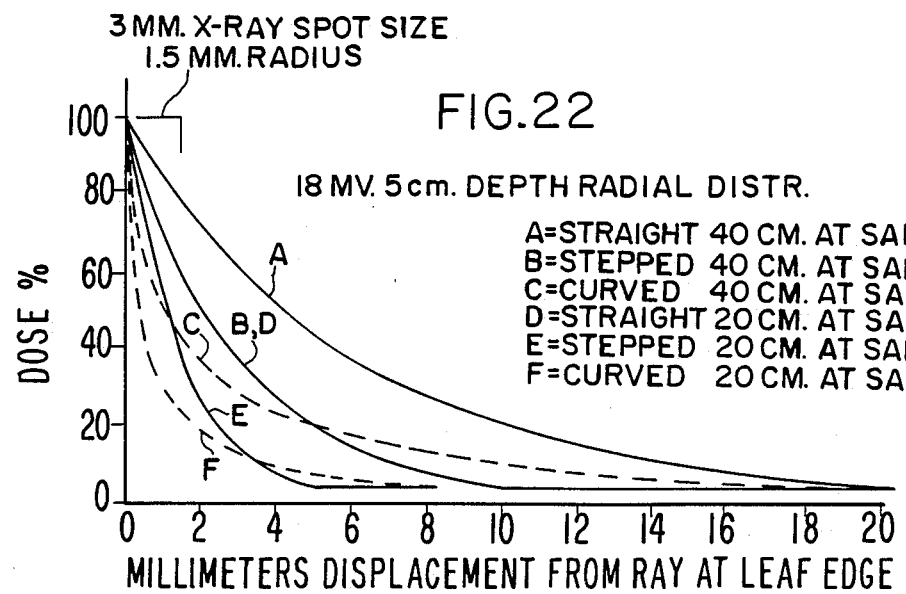
FIG. 22 is a plot of the penumbra for the configurations defined in FIG. 21.

In one embodiment of the invention, forty leaves on 1 cm pitch (at SAD) are mounted on each of two support frames. The ends of the leaves are curved with the maximum radius that maintains the ends tangent to rays from the x-ray source over the full range of travel of the leaves. The curvature of the ends of the leaves is not necessary in the fan beam mode of operation, but is necessary in the standard mode of operation with the jaws defining a wide field. The method of selecting a specific design is shown in FIGS. 21–22. Two cases of field width are considered, 40 cm (SAD) and 20 cm (SAD). Three geometries are considered for each, straight end as in A and D, stepped end as in B and E, and curved end as in C and F. Leaf transmission is less than 5%. Rays are shown in FIG. 21 to illustrate how rays are tangent at various extensions for curved ends. Ray "a" is the situation where the leaf is retracted from mid-plane; the ray is tangent on the lower part of the leaf. Ray "b" is shown for the leaf at mid-plane; this ray is tangent at the center of the leaf. Ray "c" illustrates the situation when the leaf is extended beyond midplane; the ray is tangent on the leaf nearer the top of the leaf. The graphs in FIG. 22 show calculated fall-off of radiation near the edge of the leaf for the six different cases A–F. Cases A and D, straight ends, smear the radiation near the edge of the leaf due to radiation penetrating the sharp corners. Cases B and E, stepped ends, are better. Cases C and F show approximately optimum curvature at 12.5 cm radius for 40 cm field and 25 cm radius for 20 cm field with acceptable falloff in both cases, since there are significantly larger contributions to total penumbra, such as due to radiation scatter in the patient. For additional information on the calculational technique see: Mohan et al., "Use of Fast Fourier Transforms in Calculating Dose Distributions for Irregularly Shaped Fiels for Three Dimensional Treatment Planning," Med.Phys. 14(1), pp.70-77, 1987.

FIGS. 23-28 show the MLC system mechanical arrangement. The leaves 156 and their drive systems 158 are mounted on support frames 160 which are driven by motors 162 and threaded shafts 164. The leaves in this embodiment, as shown in FIGS. 26-27, are slightly thicker at the lower edge than at the top in order to make their sides parallel to the beam rays. A step in the middle of the sides is used to block radiation in the gap between leaves. The ends of the leaves are rounded.

In normal multileaf operation, the support frames 160 are driven in synchronism with the collimator jaws 166 and the leaves 156 are individually motor driven to project into the rectangular field to produce irregular fields. In fan beam operation one support frame 160a is driven to position its set of leaves 156 close to the fan beam and the leaves 156 are individually driven into the fan beam to partially or fully block individual radiation pixel portions of it. The second support frame 160b is fully retracted and its MLC leaves 156 are individually driven to position each attached compensator finger 92.

A compensator finger 92 is attached to each leaf 156 of the second set of leaves of the multileaf system as shown in FIGS. 23-24. Each tungsten compensator finger 92 is approximately 12.7 cm long, 0.57 cm wide (tapered toward x-ray source) and about 0.9 cm high, tapering from 0.9 cm to 0.05 cm in 13 steps of 0.75 cm. The weight of each finger with its mounting step is about 0.1 kg; the weight of 40 compensator fingers, 4 kg (8.8 pounds). The compensator finger 92 is slipped onto a Tee-shaped bar 94 at the bottom of the MLC leaf 156 and is held in either a storage or operational position by detents 102. The compensator finger shape is stepped or otherwise contoured to provide an additional increment of attenuation for each increment of insertion into the fan beam. Insertion is achieved by driving the corresponding leaf of the MLC. The compensator fingers are extended for use by hand by the operator before the treatment begins, or retracted for full MLC use. It is not contemplated that full MLC mode of operation and compensator fingers would be mixed in one treatment. If it were desirable to mix these modes, solenoids could be added to retract or activate the use of the compensator fingers. For example, the transmission can be decreased in steps of 4% of open field dose rate for each 0.75 cm of insertion at a distance from the x-ray source where the fan x-ray beam is less than 0.6 cm thick, dropping transmission from 100% to 50% in 13 steps of 4% each through 9.75 cm insertion.

A 15 cm depth of absent tissue will require about 50% reduction in dose rate in that region of the field, requiring a maximum of about 0.9 cm thickness of tungsten in the compensator. The dynamic compensator can also serve as a superior wedge filter, with wedge tilt in any direction relative to the scanned field shape with more precise match of filter and tissue topography. In conventional therapy, a 60° wedge is rarely required (one rare use being for two small fields 60° apart for treatment of a shallow tumor in the brain). One documented typical usage of wedge filters was determined as 47%, none; 24%, 15°; 24%; 30°; 5%; 45°; about 0%; 60°. A 15 cm wide 45° wedge filter should produce a relative attenuation from one side to the other side of the field corresponding to 15 cm thickness from absent tissue. A 60° wedge field can be obtained with the same maximum thickness of the same material over an 8 cm field width.

Figure 29:
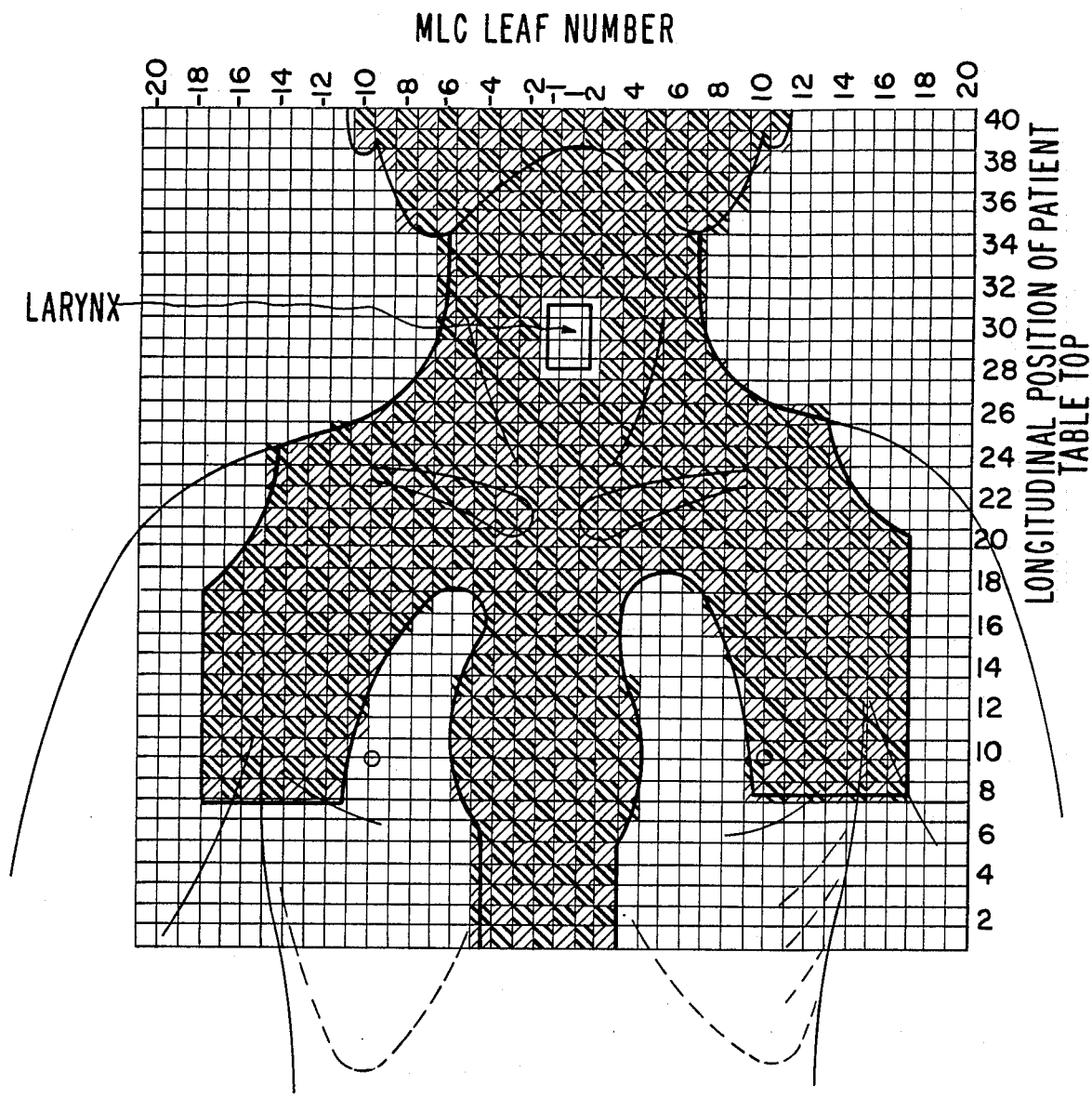
FIG. 29 is a diagram of a radiation treatment plan which is possible using the invention.
Figure 30:
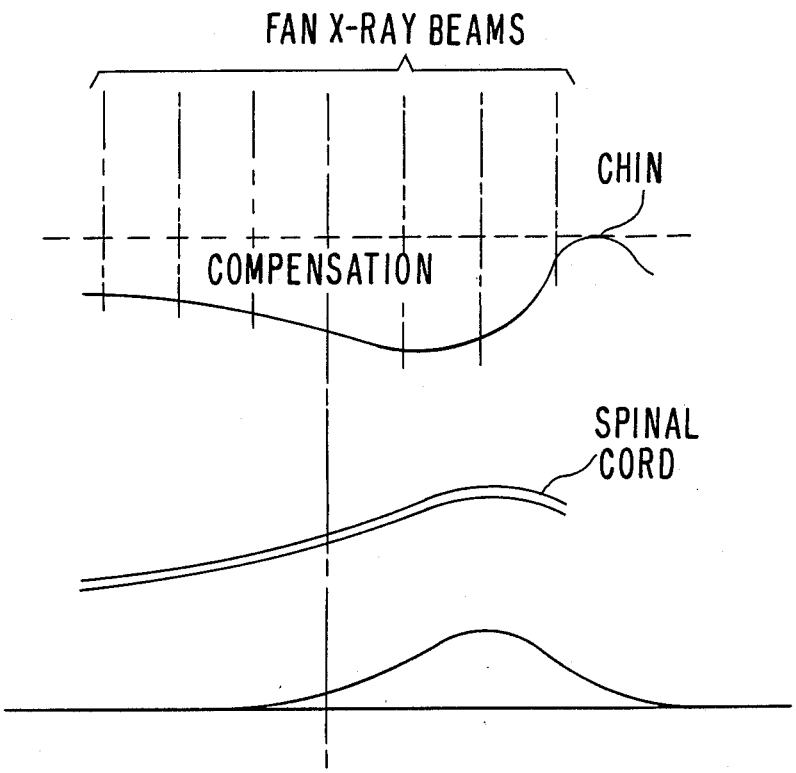
FIG. 30 is a longitudinal section through the subject of the diagram of FIG. 29.
Figure 31:
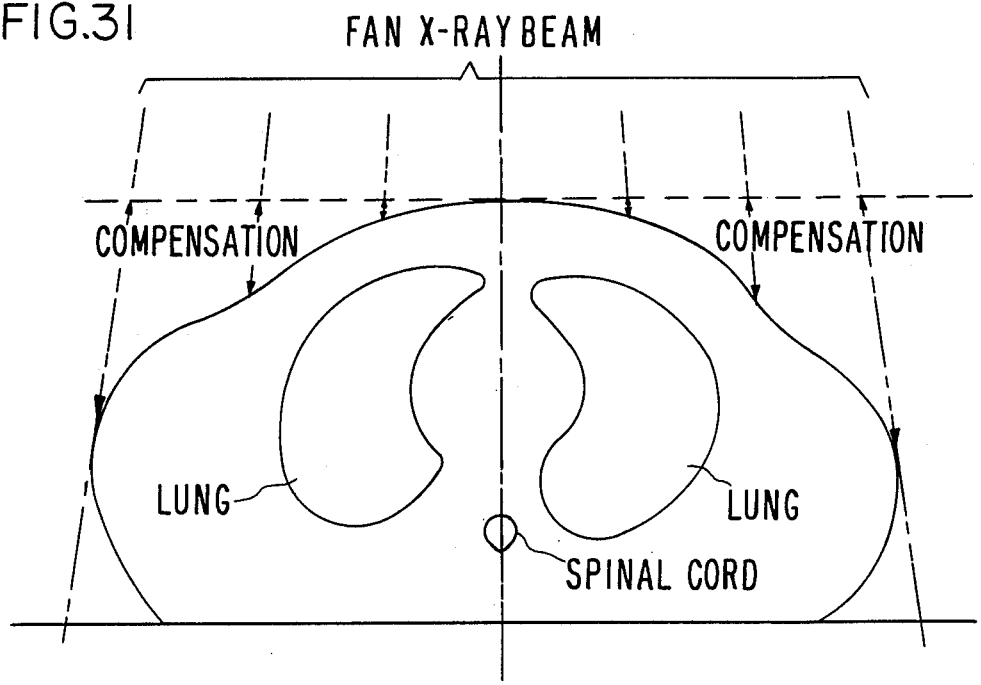
FIG. 31 is a cross section diagram through the subject of the diagram of FIG. 29.

FIGS. 29-31 illustrate the use of the fan x-ray beam with MLC leaves to define inner and outer edges of the radiation field, in this case to protect the lungs and the larynx, and with compensator fingers to compensate for the variations in depth from patient surface to midplane. With opposing beam irradiation (gantry at 0° and 180°), a uniform dose is thereby produced at the patient mid-plane. FIG. 30 is a diagram of a longitudinal view of a patient in the region from the chest through the chin showing the regions in which compensation should be used with amounts of compensation being proportional to the distance from the horizontal reference plane to the surface of the body. FIG. 31 is a related section through the chest cavity showing the amount of compensation needed and the location of the lungs. FIG. 29 shows a treatment plan for the lymph nodes in the throat and upper chest. Each square of the grid is a radiation pixel. Down the page the grid is formed by movement of the patient table through the fan beam. Across the page, the grid is formed by the MLC leaves. The cross-hatched region is the desired region to be treated. It is desired to block the radiation completely from the lungs and the larynx. These areas are shown in white; leaves would be inserted over the lungs and the larynx when the fan beam is over these. In the remainder of the crosshatched area the compensator fingers are used to adjust the dose to each radiation pixel.

In summary, a 13 step compensator finger with maximum thickness of 0.9 cm (0.35) inch) of tungsten should be adequate for both dynamic compensation and for wedge filtering in any orientation without rotation at angles up to 30° for 25 cm field, to 45° for 15 cm field, to 60° for 8 cm field dimension. An adequate profile of step thicknesses is listed below, assuming linear attenuation coefficient for tungsten of 1/12.17 mm at MeV and 1/13.46 mm at 18 MeV.

| Step | Thickness of Tungsten (mm) | 6 MeV X-ray Transmission | 18 MeV X-ray Transmission |
|---|---|---|---|
| 0 | 0.00 | 100% | 100% |
| 1 | 0.50 | 96% | 96.4% |
| 2 | 1.01 | 92% | 92.8% |
| 3 | 1.56 | 88% | 89.0% |
| 4 | 2.12 | 84% | 85.4% |
| 5 | 2.72 | 80% | 81.7% |
| 6 | 3.34 | 76% | 78.0% |
| 7 | 4.00 | 72% | 74.3% |
| 8 | 4.69 | 68% | 70.6% |
| 9 | 5.43 | 64% | 66.8% |
| 10 | 6.22 | 60% | 63.0% |
| 11 | 7.06 | 56% | 59.2% |
| 12 | 7.96 | 52% | 55.4% |
| 13 | 8.93 | 48% | 52.5% | thickness of the fan x-ray beam can be set precisely to 1 cm or 0.5 cm by closing the lower set of collimator jaws onto shims which are flipped into place outside the 40 cm (SAD) edges of the fan when switching to fan mode. This avoids variations in opening of the jaws due to their weight as the gantry is rotated. This is important in maintaining a constant dose rate as a base, from which variations can be made with the compensator fingers.

The patient table can be stepped longitudinally in 1 cm steps, with the beam switched off for 0.1 second during each 1 cm of movement at 10 cm/second and switched on for 1 second of dwell time at each step with 1 cm thick fan beam, and correspondingly for 0.5 cm steps and fan beam. A ratchet can be added to the patient table to make these steps precise. Setting of the MFL leaves at each patient table step, including those at the ends of the field, will define the longitudinal boundaries of irradiated regions. 10 cm per second velocity corresponds to about 0.2 miles per hour so patient vibrations can be minimal and patient comfort can be achieved. However, this will produce regions of underdose at shallow depths and overdose at large depths at the 1 cm longitudinal intervals in the step-scanned field. These dose variations tend to cancel out with opposing beams (e.g., 2, 4 or 6 ports at 180°, 90° or 60°, but not as well with non-opposing beams.

The patient table can be moved continuously at constant speed (of 1 cm/second) longitudinally, eliminating the longitudinal variations in dose. Penumbra at longitudinal edges at one end of irradiated areas can then be minimized by opening (withdrawing) the first set of appropriate MLC leaves at 1 cm/second (SAD) at the start of each irradiation area. Similarly, on reverse scan these MLC leaves will be closed (inserted) at 1 cm/second at the end of each such irradiation area. These counteractive movements locate the irradiated region longitudinal edge to the patient's anatomy at that one end. At the other end of irradiated areas, the resulting penumbra (80% to 20% dose) will be enlarged from about 7 mm to 12 mm. Where small penumbra longitudinally is essential at the opposing end of irradiated regions as well, a 0.5 cm fan x-ray beam can be formed by the lower collimator jaws even for fields longer than 20 cm, at least in such regions.

In the alternative where the patient table is stepped longitudinally, the MLC leaf speed should be about 10 cm/second at SAD to be able to move fully in or out of the fan x-ray beam in the 0.1 second beam off time in which the patient table is stepped. Similarly, the compensator fingers should be able to move by one 0.75 cm longitudinal step of 4% dose increment in this 0.1 second beam off time. Thus, one set of MLC leaves should be able to move at 10 cm/second over steps of 1 cm at a time, the other set of MLC leaves with compensator fingers at 7.5 cm/second over steps of 0.75 cm at a time, all at SAD. In the alternative where the patient tables moves continuously, the radiation beam can remain on and the MLC leaves, with or without compensator fingers, can move more slowly, at 3 cm/sec at SAD, for example.

FIG. 32 shows a block schematic of an electronic system to drive: (1) the MLC support frames; (2) the first set of MLC leaves for shaping field inner and outer edges; (3) the second set of MLC leaves with compensator fingers attached, which control the radiation intensity distribution within the field.

There is an independent controller for each motor 158 or 162. Each pulse of current from the controller causes the motor to rotate sufficiently to increment its corresponding MLC leaf position by 1 mm (SAD), through rotation of its lead screw by 1 turn. A positive current pulse causes positive rotation of the lead screw; a negative current pulse, negative rotation. A counter increments or decrements its total count by one count for each positive or negative rotation, respectively, of the lead screw and returns a corresponding trigger to the controller to end that drive pulse. A comparator in the controller continues to trigger output positive or negative drive current pulses to the motor until the count value from the lead screw counter and the position value from the treatment plan are equal for the corresponding radiation pixel of the treatment field.

MLC leaf and compensator finger positions are independently confirmed by a TV camera 168 which views index marks on each leaf and finger via lens 170 and appropriately positioned mirror 172 in the radiation head, as shown for example in FIG. 24.

The treatment plan is stored in computer random access memory. For example, for each field the following parameter values will be stored (collimator angle and patient table angle and MLC support frame positions will be set at standard values):

| Gantry angle | (Selected fixed value) |
|---|---|
| Lower jaws. Symmetrical opening | (0.5 or 1 cm SAD) |
| Dose monitor units per second | (Selected fixed value) |
| Patient table top longitudinal limits | (Start/stop) |
| Patient table top longitudinal speed | (Selected fixed value) |
| Patient table top vertical position | (Selected fixed value) |
| Patient table top lateral position | (Selected fixed value) |
| For each of N longitudinal positions of patient table top: | |
| Step position of each of 40 MLC leaves (out/half/in) | |
| Step position of each of 40 compensator leaves (0,1,12,13). | |

N can be for example 40 equally spaced longitudinal positions of the patient table top at 1 cm intervals over a 40 cm long field. The table top moves continuously at constant speed and at each of the N positions the corresponding values for the compensator fingers and MLC leaves are sent to the comparators in their drive motor controllers.

The inner and outer boundaries of the treatment field from the treatment plan and from the TV camera are displayed in two colors on a storage CRT at each longitudinal cm of field length. Any difference between the two displays exceeding 2 mm triggers an interlock which can be used to interrupt irradiation.

In addition to dynamically compensated fan x-ray mode, irregular field multileaf x-ray mode, conventional shadow blocked rectangular x-ray field mode, and conventional electron therapy mode are retained.

In electron mode at typical maximum rating of 500 cGy/minute, the average electron current at SAD is approximately $4.6 \times 10^{-11}$ ampere per $cm^2$, $3 \times 10^{-8}$ ampere in a $25 \times 25$ cm electron field. The average electron current at the electron scattering foils is approximately 5 times higher, or $1.5 \times 10^{-7}$ ampere. A detector capable of sensing $3 \times 10^{-7}$ ampere average current with a precision of $1 \times 10^{-7}$ ampere and operating an interlock within one interpulse time to terminate the klystron modulator trigger at this value will protect the patient from receiving an electron dose rate of more than approximately twice rated maximum, provided that the electron scattering foils are intact. Since the average electron current at the x-ray target in fan x-ray beam mode at 3000 cGy/minute is approximately $4 \times 10^{-4}$ ampere at 6 Mev, if it reached the patient, it will deliver a dose rate of $1.1 \times 10^4$ cGy per second. Hence, such a sensor/interlock is required to protect the patient in the unlikely event of x-ray mode accelerator current with x-ray target retracted, electron scatterer in the beam instead of x-ray flattening filter, and failure of the ionization chamber to operate its interlocks to terminate irradiation in of the order of 0.01 second.

At $3 \times 10^{-7}$ ampere average current and 0.005 beam duty cycle, the pulse current at the electron window is 0.6 milliampere. A pulse toroid can produce a 60 millivolt pulse across a 100 ohm load. A change of 0.1 milliampere pulse current will be detectable reliably (99% confidence level) in a noise level of 3 millivolts.

Bess, et al. describes a toroid monitor for linac beam current which had a pulse current sensitivity of 0.5 mA. (See: Bess, et al., 1959, "External Beam Current Monitor For Linear Accelerators", *Rev. Sci. Inst.*, 30, pp. 985–988.) Bess, et al., states that this sensitivity can be increased to 0.05 milliampere. The monitor includes a calibration loop to simulate the linac beam current. Menke describes a toroid beam current monitor with pulse current sensitivity of 0.02 milliampere and noise level of 2 millivolts. (See: Menke, 1969, "Beam Monitoring at the NBS Linac - Energy, Positioning, Current, Charge", *IEEE Trans. on Nuclear Science*, NS-16, #3, pp. 921–922.) In both cases, the toroid core aperture diameter was about 5 cm, the core cross-section about 5 cm$^2$ and beam current range 100 to 1. In the present application as a sensor for an interlock, linearity is desired only up to a few milliamperes pulse beam current so a much smaller core cross-section can be used.

Figure 33:
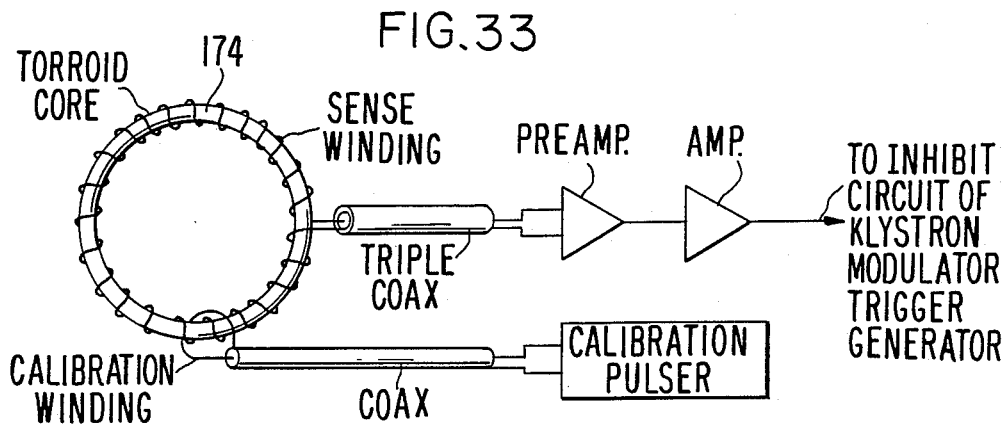
FIG. 33 shows a schematic diagram of a toroid beam pulse sensing system.
Figure 38:
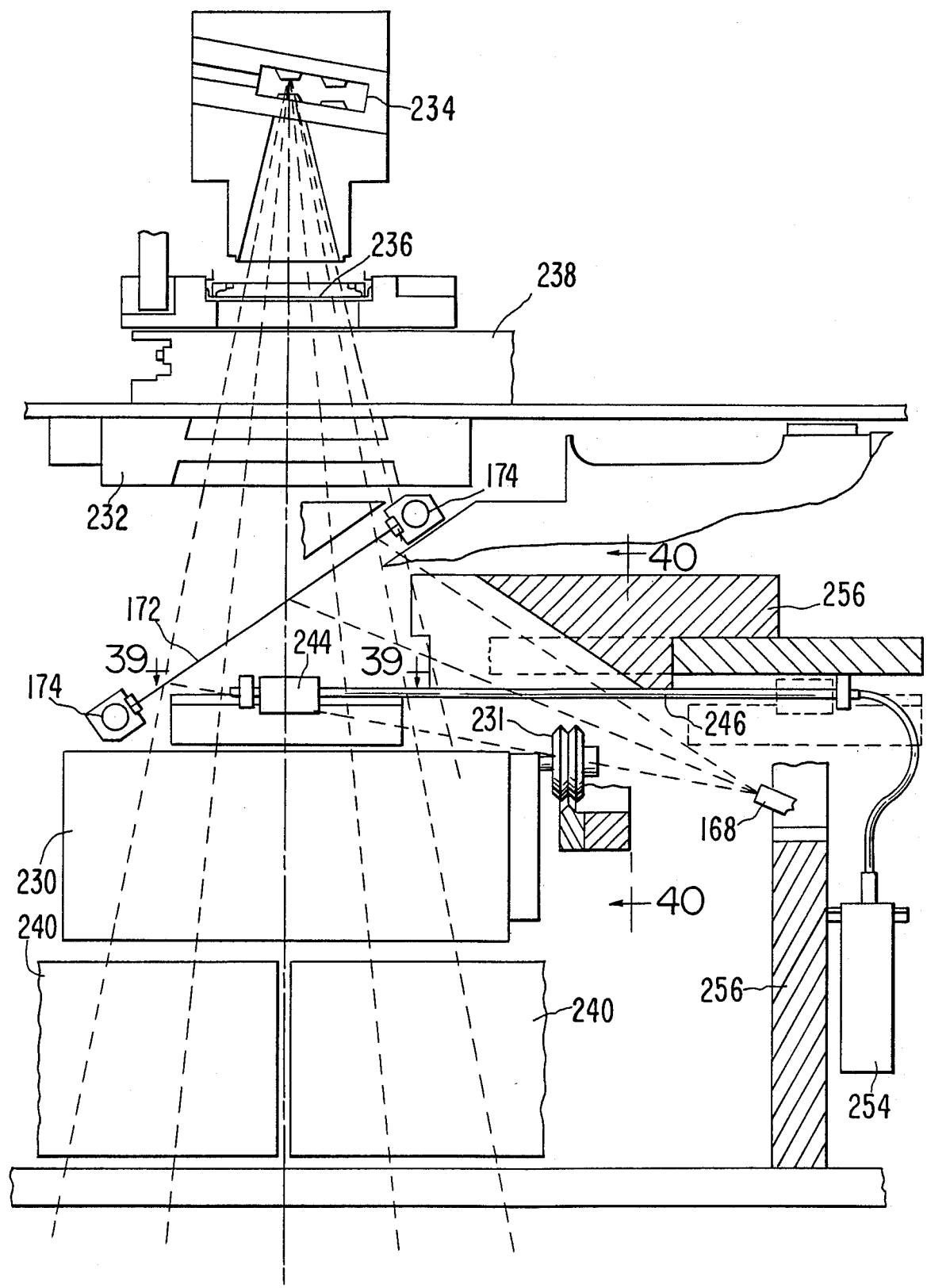
FIG. 38 shows a radiation head with insert system for conventional static compensator and automatic wedge filter and with toroid beam sensor.

FIG. 33 and 38 shows a compact toroid 174 located after the electron window. The ferrite core cross-section is about 1 cm$^2$, with single turn calibration coil and 30 turn sensor coil of insulated wire. The toroid 174 is shielded from low frequency external magnetic fields by mu-metal and from high frequency magnetic fields by a copper sheath, both of which are slotted to permit penetration by the pulse electron current magnetic field. The sense signal output is fed to an amplifier via triple coax cable.

The electron scatterer spreads the electron beam into a lobe which has a cross-section which is typically significantly smaller than the ionization chamber dose rate electrodes. If the electron scatterer fails, the lobe collapses to a still smaller diameter, increasing the dose rate in a smaller area at the patient by a factor of the order of 20 at some energies. However, the ionization chamber will record less than normal total charge because of the concentration of ionization and consequent recombination. This will result in terminating irradiation by the underdose interlock, but only after delay of about 9 seconds, which is conventionally employed to permit the accelerator dose rate to stabilize. The operator may restart irradiation a number of times (e.g., 5 times). At planned dose rate of 500 cGy/minute, but actually 20 times this value for $9 \times 5 = 45$ seconds, the patient will receive an unplanned localized dose of 7500 cGy. To avoid this type of collapsed beam overdose due to failure of the electron scatterer, a dual foil electron scatterer can be pressurized or evacuated, as shown in FIGS. 34–37, so that foil failure will cause interruption of a light beam to an interlock which terminates the klystron modulator trigger.

Figure 34:
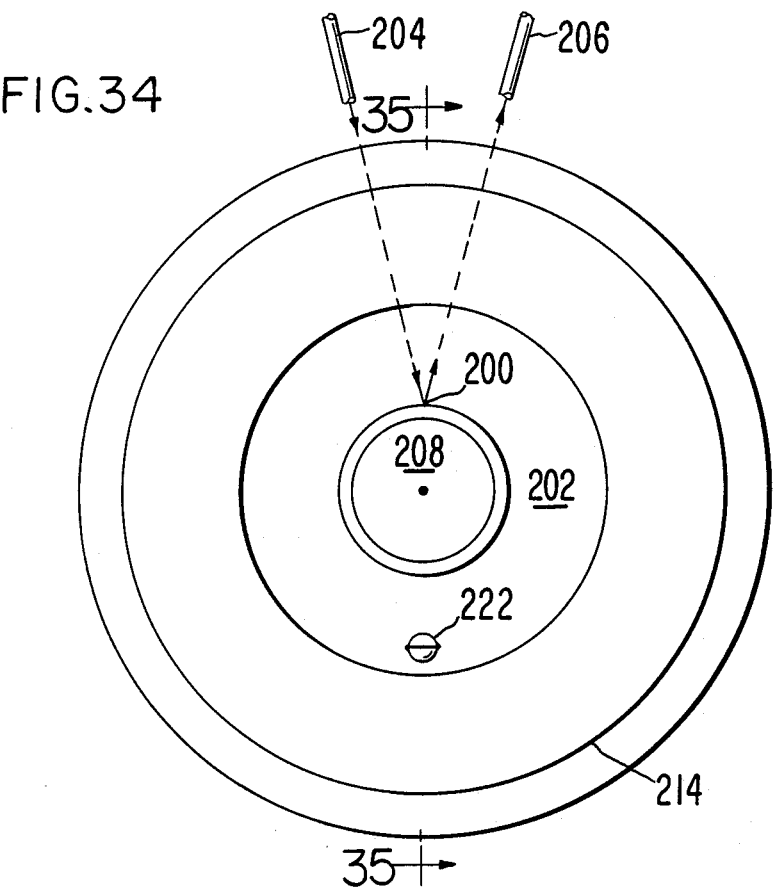
FIG. 34 shows a top view of a pressurized and interlocked dual foil electron scatterer.
Figure 35:
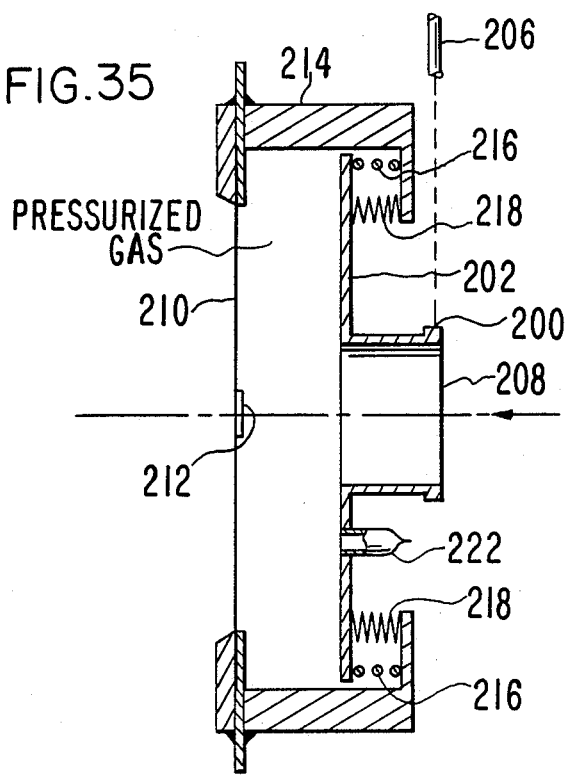
FIG. 35 is a sectional view of the device of FIG. 34 along the section line 35—35.

The pressurized and interlocked dual foil electron scatterer is shown in FIGS. 34–35. A reflective surface 200 is formed in the flange 202. A light source illuminates the reflective surface 200 through fiber optics 204. The reflection of the light is conducted through fiber optics 206 to a detector (not shown). A first foil 208 is mounted on the flange 202. A second foil 210 with button 212 is mounted on foil holder 214. A spring 216 and a bellows 218 are placed between flange 202 and a lip 220 on foil holder 214. The assembled scatterer is filled with pressurized gas through a pinch-off 222. If a foil ruptures the light beam detector will not detect the reflected beam due to the depressurization of the scatterer and collapse of the flange 202 moving the reflective surface 200.

Figure 36:
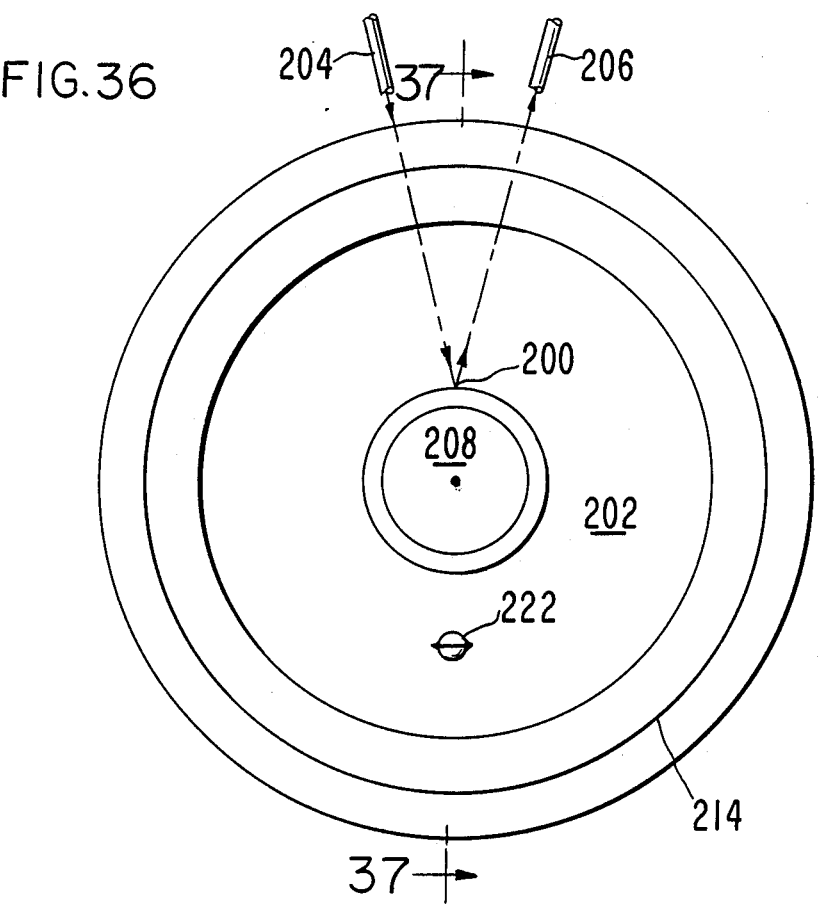
FIG. 36 is a top view of an evacuated and interlocked dual foil electron scatterer.
Figure 37:
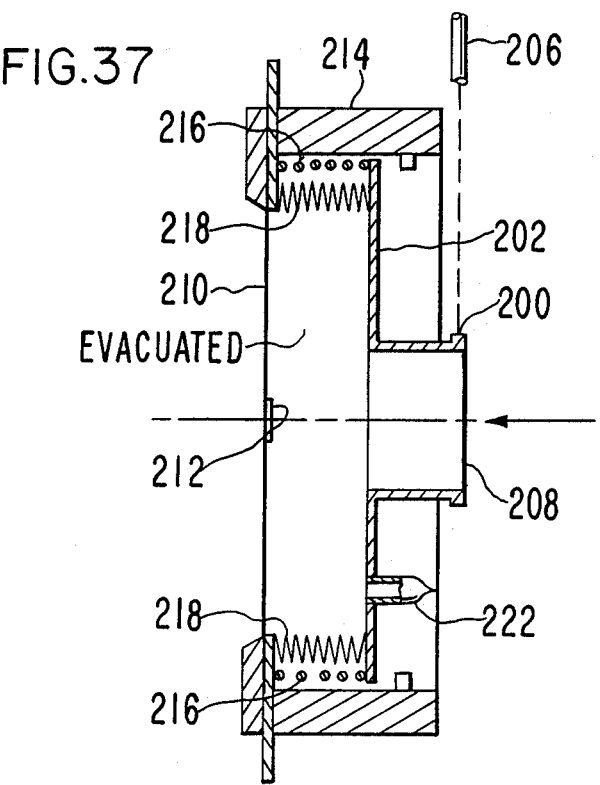
FIG. 37 is a sectional view of the device of FIG. 36 along the section line 37—37.

FIGS. 36–37 show a closely related evacuated and interlocked dual foil electron scatterer. The difference in the evacuated scatterer is in the placement of the spring 216 and bellows 218. Here rupture of the foil will cause the spring 216 to extend the flange 202 out of position, thereby interrupting the light beam.

Since the MLC is located in the region normally occupied by the wedge filter mount, just below the lower collimator jaws, it is desirable to relocate the wedge filter. Manual insertion of conventional wedge filters is time consuming so it is desirable to make insertion automatic. In machines in which only one set of collimator jaws can be driven independently, it is desirable to be able to reverse the wedge filter angle remotely, for applications such as tangential breast treatment with opposing offset wedged fields.

Figure 39:
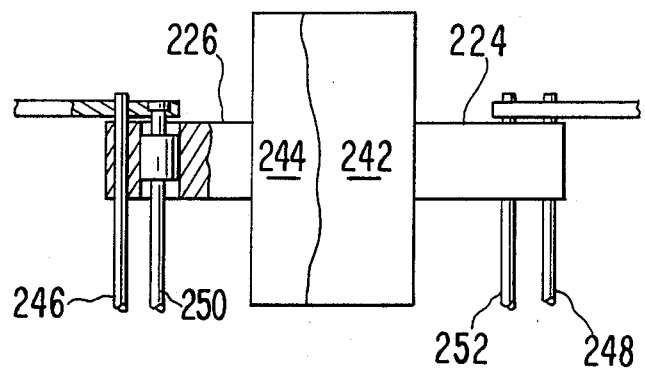
FIG. 39 is a sectional view of the system of FIG. 38 along the section line 39—39.
Figure 40:
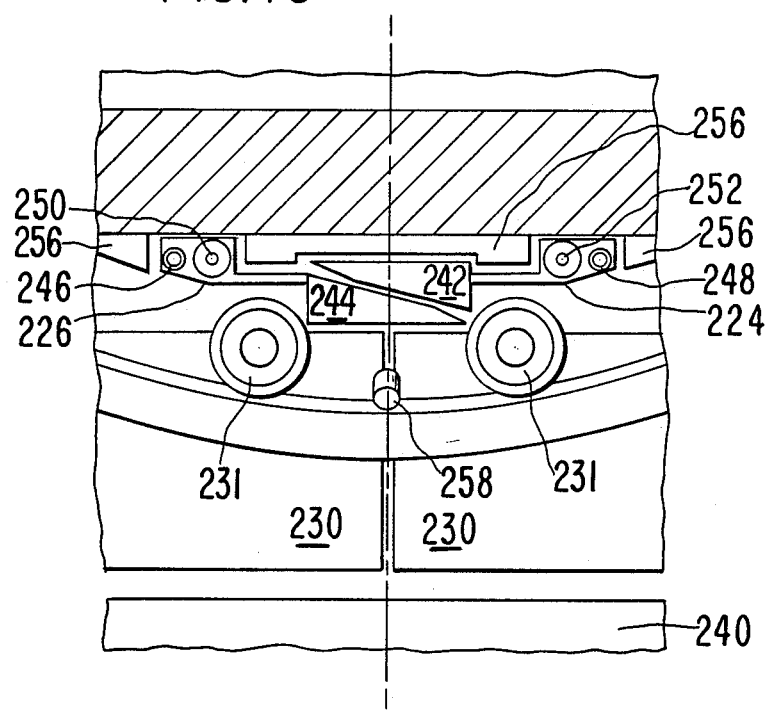
FIG. 40 is a sectional view of the system of FIG. 38 along the section line 40—40.

The wedge filter can be physically quite small if it can be located on the source side of the collimator jaws. FIGS. 38–40 show an arrangement in which two small automatically insertable trays 224,226 are located at the level of the light field mirror 172 between the upper collimator jaws 230 and the ionization chamber 232. The x-ray beam originates at the target 234, passes through the electron window 236, then passes through the carousel 238 holding the x-ray flattening filter and electron scatterers, and then passes through the ionization chamber 232. The lower jaws 240 are orthogonal to the upper jaws 230, which are movable on drive apparatus 231. A pair of wedge filters 242,244 are mounted on the trays 224,226, respectively. The trays 224,226 are slidable on support rods 246,248 and are driven by lead screws 250,252 coupled to electric motors 254. Lead shielding 256 surrounds the apparatus.

A 45° wedge filter for 20 cm field width in the wedged direction, 35 cm in the orthogonal direction can be mounted on each of these trays, the two wedge filters having their angles opposed to each other. The wedge filter thickness is 1.6 cm of tungsten. Each tray can be retracted clear of a $40 \times 40$ cm field radiation beam. One tray can be inserted for wedged fields offset from beam axis in one direction, the other tray for fields offset in the opposite direction, for example. For wedge angles less than 45°, two exposures are given per field, one with the wedge filter retracted. In those rare cases where a wedge angle greater than 45° is required, since the field width in such cases is small, a 1.6 cm thick tungsten 60° wedge can be inserted in one of the trays. Conventional custom compensators (but comprised of an assembly of small tungsten blocks of appropriately selected height) can be mounted on one of the trays instead of a wedge filter.

Two miniature permanent magnet DC motors 254 are used to move the trays 224,226 in and out via flexible cable drive. Optical interlocks confirm the inserted and retracted linear limits of each tray.

This invention is not limited to the preferred embodiment and alternatives heretofore described, to which variations and improvements may be made including mechanically and electrically equivalent modifications to component parts, without departing from the scope of protection of the present patent and true spirit of the invention, the characteristics of which are summarized in the following claims.

What is claimed is:

1. An apparatus forming an accessory and improvement to medical electron accelerators generating an x-ray fan beam, comprising:

control means for providing dynamic control of radiation dose using a collimator in a treatment volume of arbitrary external and internal shape including dynamic control of radiation varying in intensity both in space and time independently within said arbitrary external shape while treatment of a subject progresses.

2. The apparatus of claim 1 wherein said control means includes means for delivering the dose in the same parallel planes in the subject as in computed tomography imaging planes in the subject.

3. The apparatus of claim 2 including means for continuously monitoring the three-dimensional radiation dose in the subject while radiation of the subject progresses.

4. An accessory apparatus for a source of x-rays for radiation of a subject, the source of rays including x-ray blocking jaws mounted on a jaw-frame for defining a rectangular field x-ray field; the apparatus comprising:

defining means for dynamically limiting the radiation to radiation pixels while radiation of the subject progresses; and compensating means for dynamically reducing the intensity of x-rays by 1 to 95% within radiation pixels not blocked by said defining means before the x-rays reach the subject while radiation progresses;

said defining and compensating means being mounted on the jaw frames and acting in concert with the jaws.

5. The apparatus of claim 4 wherein said defining means includes means for dynamically blocking at least 95% of the x-rays within a given radiation pixel before they reach the subject.

6. The apparatus of claim 5 including means for continuously monitoring the three-dimensional radiation dose in the subject while radiation of the subject progresses.

7. An apparatus acting as a collimator in a radiation therapy machine having jaws mounted in a jaw frame for limiting a fan beam x-ray radiation field to rectangular boundaries, comprising:

leaf means for further blocking and shaping a radiation field within the rectangular boundaries, said leaf means including a multiplicity of straight leaves opaque to x-rays;

mounting means for mounting said leaf means on the jaw frame, said mounting means including leaf support frame assemblies;

drive means for providing motion of said leaf means relative to said leaf support frame assemblies and for motion of said leaf support frame assemblies relative to the jaw frame; and compensator means for adjusting the intensity of the x-rays at the subject within the radiation field defined by the jaws and leaf means, said compensator means being independently insertable into the radiation field.

8. The apparatus of claim 7 wherein said compensator means is retractably supported on said leaf means.

9. The apparatus of claim 7 in which said leaf means are a matched pair of leaf sets, each leaf set including a multiplicity of leaves, each one of said pair having means for insertion from opposite sides of the x-ray therapy beam.

10. The apparatus of claim 9 in which said compensator means is movably attached to one of said pair of leaf sets.

11. The apparatus of claim 10 in which said compensator means includes compensator fingers, one compensator finger being movably attached to each leaf.

12. The apparatus of claim 11 wherein each compensator finger is tapered.

13. The apparatus of claim 12 wherein each tapered compensator finger is tapered in steps.

14. The apparatus of claim 7 including a detector means for confirming the shape and dose distribution of the radiation field relative to the subject.

15. The apparatus of claim 7 including a self-shielded x-ray fan beam flattening filter.

16. The apparatus of claim 7 including a pressurized interlocked dual electron scattering foil.

17. The apparatus of claim 7 including means for moving the subject along an axis perpendicular to the plane of the fan beam.

18. The apparatus of claim 7 including means for automatic insertion of a static wedge filter and static compensator in the x-ray beam before the beam passes said leaf means.

19. A method of operating a radiation therapy machine comprising the steps of:

(a) limiting the radiation field to a fan beam using two orthogonal pairs of jaws of radiation opaque material;

(b) dynamically further limiting the radiation field using a multiplicity of straight leaves of radiation opaque material, said leaves being mounted in a first of a pair of leaf support frame assemblies which are independently movable relative to the jaws;

(c) dynamically limiting the radiation intensity within the radiation field by means of compensators mounted to leaves in a second of a pair of leaf support frames, said step being performed simultaneously to step (b);

(d) moving a table holding a patient along an axis perpendicular to the fan beam in accordance with a patient treatment plan, said step being performed simultaneous with steps (b) and (c).

20. An irradiation treatment method comprising:

(a) causing an irradiation source to emit a two-dimensional radiation fan beam in a first plane;

(b) controlling the location of matter to be treated by irradiation by said fan beam so that said matter is movable along a line which is perpendicular to the plane of said fan beams;

(c) interposing an adjustable means for shaping the beam and controlling the beam intensity between said matter to be irradiated and said irradiation source;

(d) calculating a desired shape and intensity distribution for the portion of said fan beam which impinges on said matter for each position of said matter along said line so that the fan beam radiation which falls on said matter selectively irradiates a preselected volume of said matter with a preselected intensity distribution;

(e) causing said adjustable means for shaping the beam and controlling the beam intensity to be adjusted responsive to said calculated desired beam shape to form a shaped and modulated beam; and (f) irradiating said matter in said plane with said shaped and modulated beam by causing said source to emit radiation.

21. The method of claim 20 wherein said matter is moved in discrete steps along said line.

22. The method of claim 21 wherein steps (e) and (f) are repeated for each said discrete portion of said matter to be treated in order to controllably provide a selectable amount of radiation to a selected portion of the volume of said matter to be treated.

23. The method of claim 22 wherein the matter to be treated is a biological sample containing cancerous cells to be irradiated.

24. An apparatus for radiation of a subject, comprising:

an electron accelerator source of x-ray beams, said accelerator being mounted in a gantry for changing the direction of incidence of x-ray beams on a subject, a subject holding table, said subject holding table including means for moving the subject along a line relative to the x-ray beam, defining means for dynamically limiting the radiation to radiation pixels while radiation of the subject progresses;

compensating means for dynamically reducing the intensity of x-rays by 1 to 95% within radiation pixels not blocked by said defining means before the x-rays reach the subject while radiation progresses, and computer means for controlling said accelerator, said table, said defining means and said compensating means in accord with a programmed plan.

25. The apparatus of claim 24 wherein said defining means includes means for dynamically blocking at least 95% of the x-rays within a given radiation pixel before they reach the subject.

26. The apparatus of claim 25 including means for continuously monitoring the three-dimensional radiation dose in the subject while radiation of the subject progresses.

* * * * *